US012114878B2

(12) United States Patent
Horowitz et al.

(10) Patent No.: US 12,114,878 B2
(45) Date of Patent: Oct. 15, 2024

(54) DEVICES AND METHODS FOR REPAIRING A PATHOLOGICAL CONNECTION BETWEEN TWO ANATOMICAL STRUCTURES

(71) Applicant: Retriever Medical, Inc., Las Vegas, NV (US)

(72) Inventors: Michael Bruce Horowitz, Naples, FL (US); Benjamin William Bobo, Las Vegas, NV (US); Brandon Matthew Repko, Mars, PA (US)

(73) Assignee: Retriever Medical, Inc., Las Vegas, NV (US)

( * ) Notice: Subject to any disclaimer, the term of this patent is extended or adjusted under 35 U.S.C. 154(b) by 367 days.

(21) Appl. No.: 17/809,528

(22) Filed: Jun. 28, 2022

(65) Prior Publication Data

US 2023/0015203 A1    Jan. 19, 2023

Related U.S. Application Data

(63) Continuation-in-part of application No. 17/572,206, filed on Jan. 10, 2022, now Pat. No. 11,589,881, and a continuation-in-part of application No. 17/572,138, filed on Jan. 10, 2022, now Pat. No. 11,382,643, said application No. 17/572,206 is a continuation of (Continued)

(51) Int. Cl.
*A61B 17/22*      (2006.01)
*A61B 17/221*    (2006.01)
*A61B 17/00*      (2006.01)
*A61M 25/10*     (2013.01)

(52) U.S. Cl.
CPC ...... *A61B 17/22032* (2013.01); *A61B 17/221* (2013.01); *A61B 2017/00867* (2013.01); *A61B 2017/22038* (2013.01); *A61B 2017/22051* (2013.01); *A61B 2017/22054* (2013.01); *A61B 2017/22072* (2013.01); *A61B 2017/22079* (2013.01); *A61B 2017/22094* (2013.01); *A61M 2025/1013* (2013.01); *A61M 2025/1015* (2013.01)

(58) Field of Classification Search
None
See application file for complete search history.

(56) References Cited

U.S. PATENT DOCUMENTS 10,172,634 B1    1/2019    Horowitz

FOREIGN PATENT DOCUMENTS

WO    WO-2014/165023 A1    10/2014
WO    WO-2018/156962 A1    8/2018
WO    WO-2021/011801 A1    1/2021

*Primary Examiner* — Richard G Louis
(74) *Attorney, Agent, or Firm* — Francis Law Group

(57) ABSTRACT

A device is disclosed for occluding an anatomical passage between first and second anatomical structures. The device includes a tip portion having a proximal element connected to a distal element through a member. The proximal element and/or distal element is movable axially along the tip portion while the other element preferably remains fixed in place. A handle is coupled to a proximal end of the tip portion through a shaft. The tip portion is positioned across the anatomical passage so that the proximal element occludes a first side of the passage and the distal element occludes a second side of the passage. A locking structure, such as a nut, is positioned or crimped against the proximal element, and, once done, the tip portion is released at the occluded passage.

20 Claims, 24 Drawing Sheets

Related U.S. Application Data application No. 17/450,978, filed on Oct. 14, 2021, said application No. 17/572,138 is a continuation of application No. 17/450,977, filed on Oct. 14, 2021.

(60) Provisional application No. 63/364,168, filed on May 4, 2022, provisional application No. 63/268,094, filed on Feb. 16, 2022, provisional application No. 63/260,406, filed on Aug. 19, 2021, provisional application No. 63/215,724, filed on Jun. 28, 2021, provisional application No. 63/215,565, filed on Jun. 28, 2021, provisional application No. 63/215,579, filed on Jun. 28, 2021, provisional application No. 63/215,587, filed on Jun. 28, 2021, provisional application No. 63/215,583, filed on Jun. 28, 2021, provisional application No. 63/215,573, filed on Jun. 28, 2021, provisional application No. 63/092,428, filed on Oct. 15, 2020.

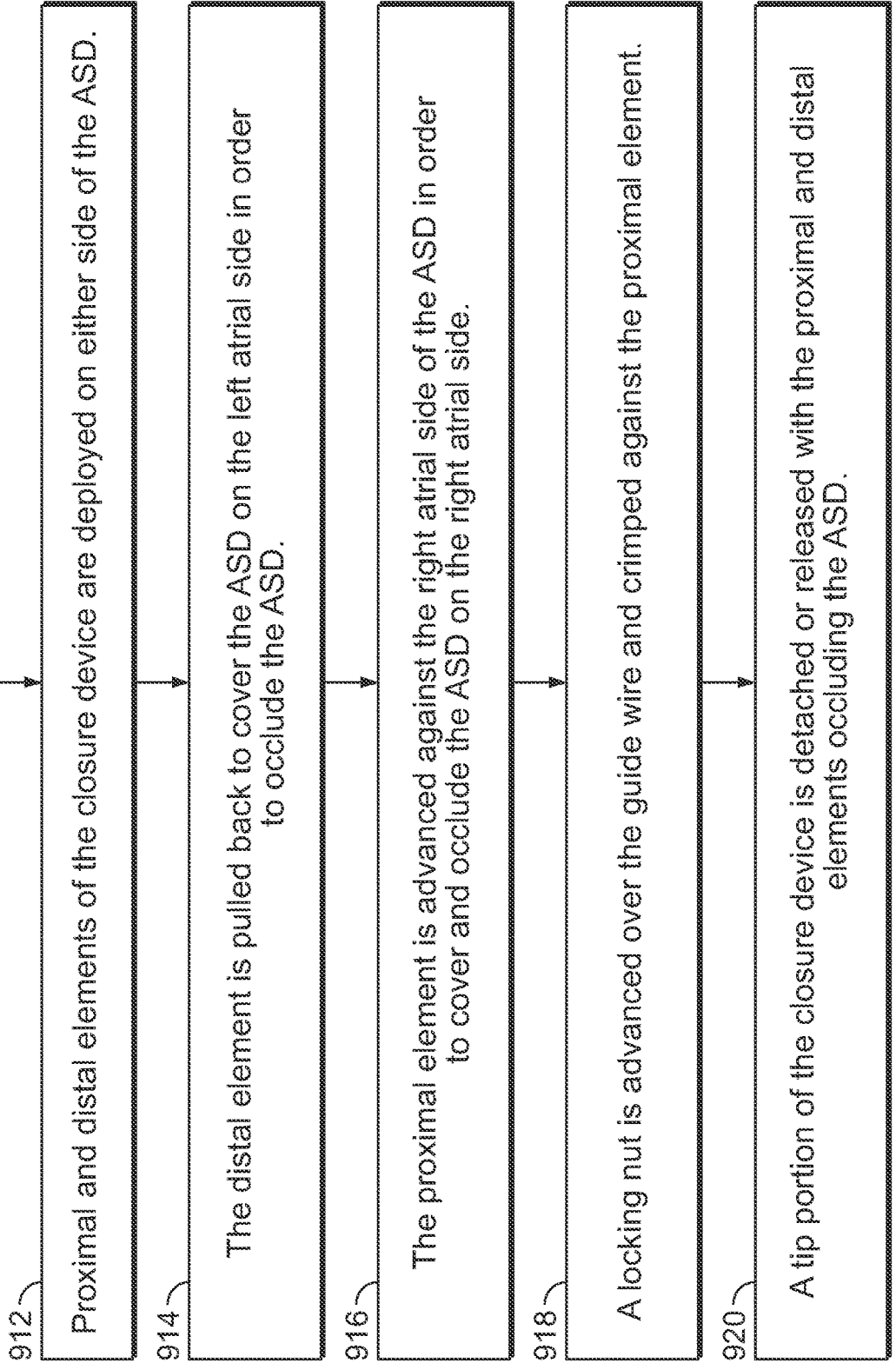

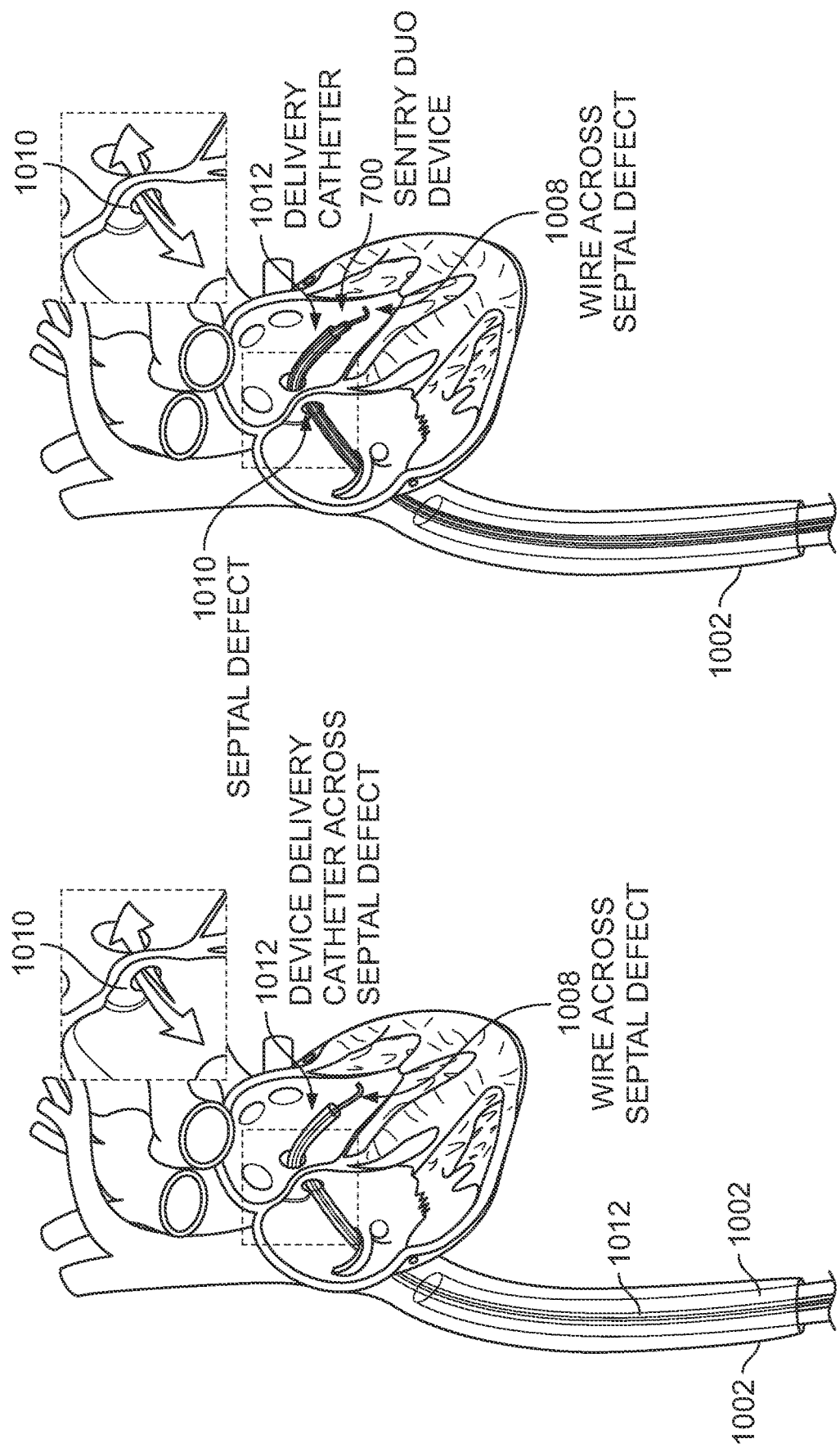

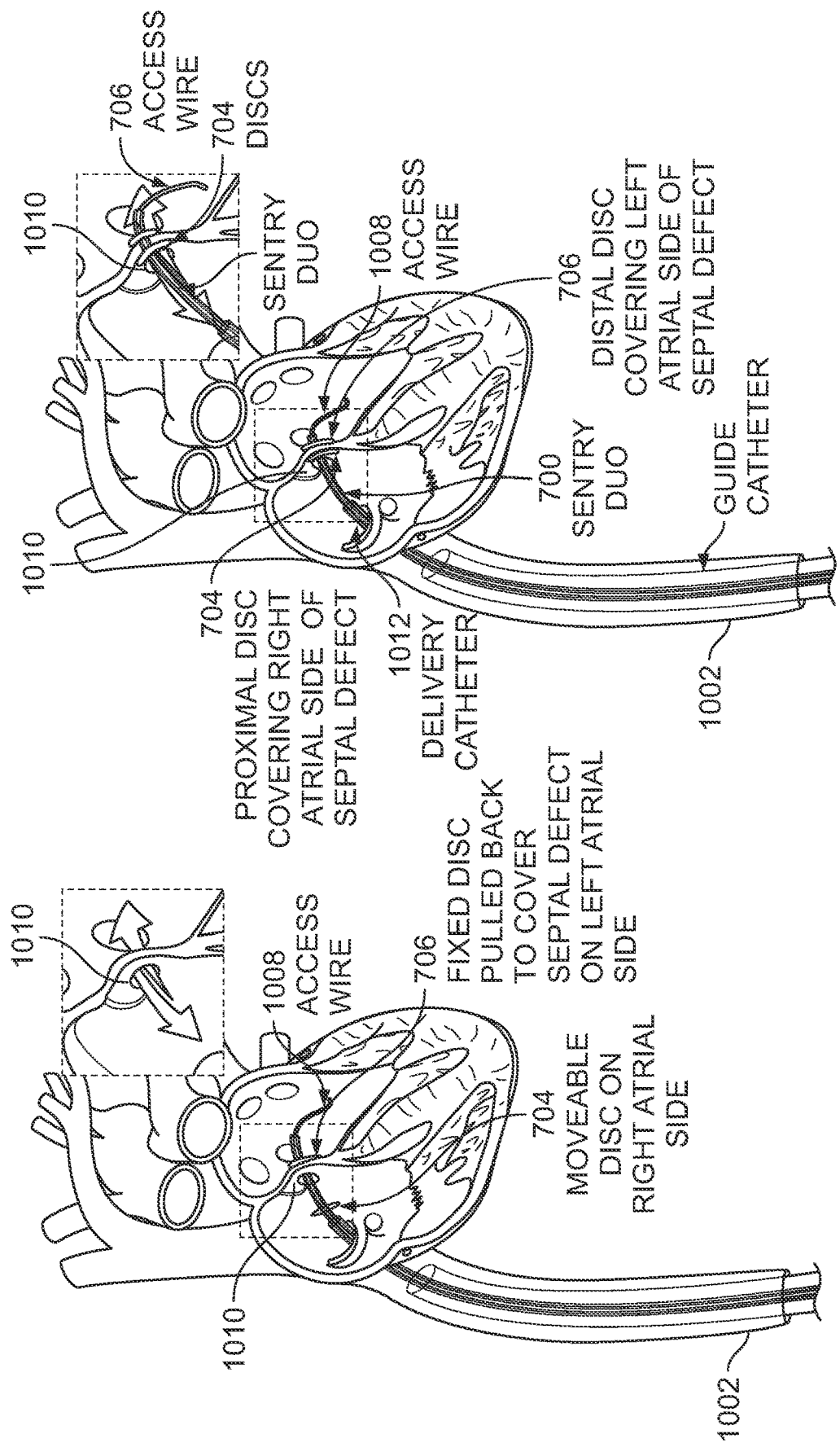

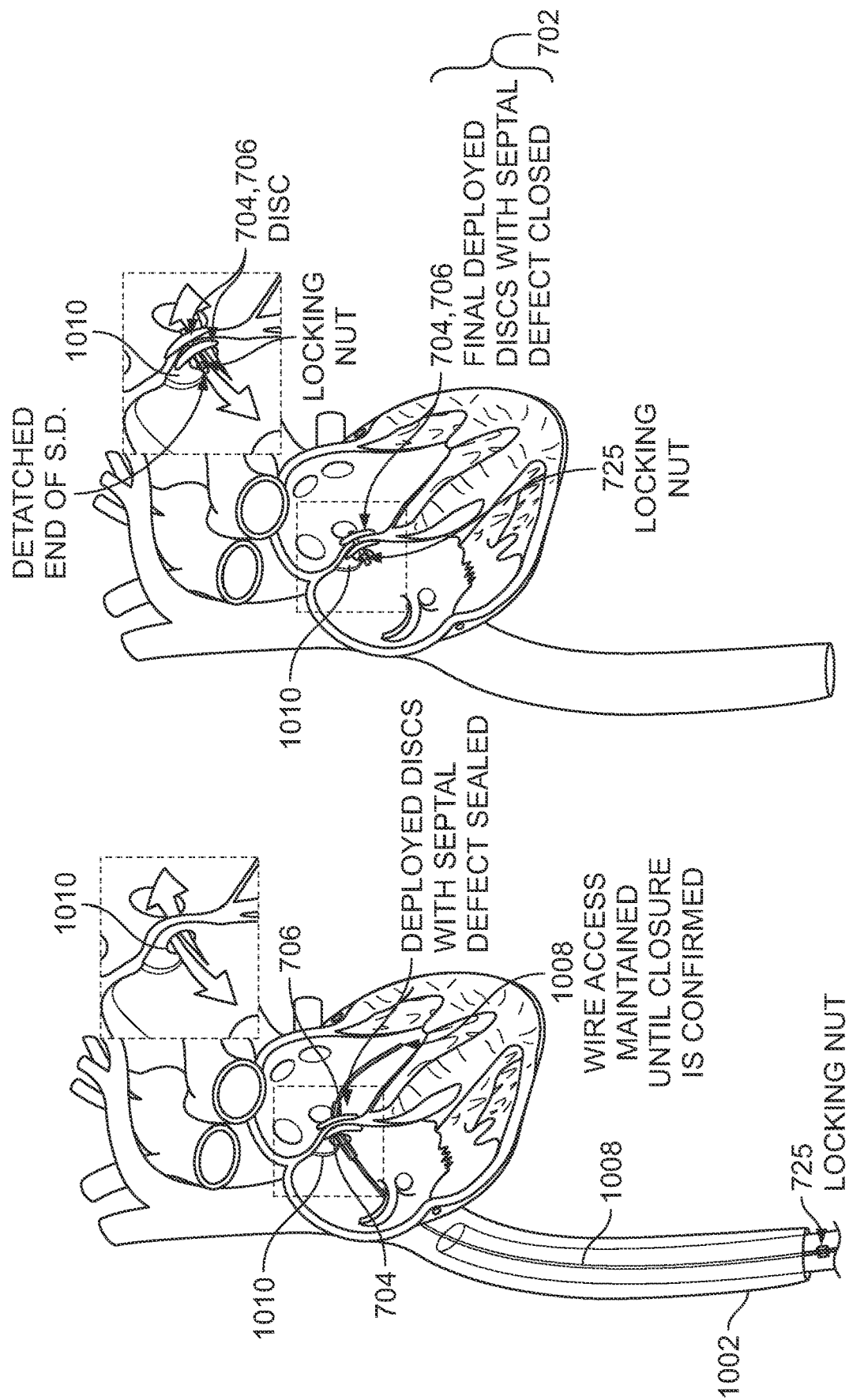

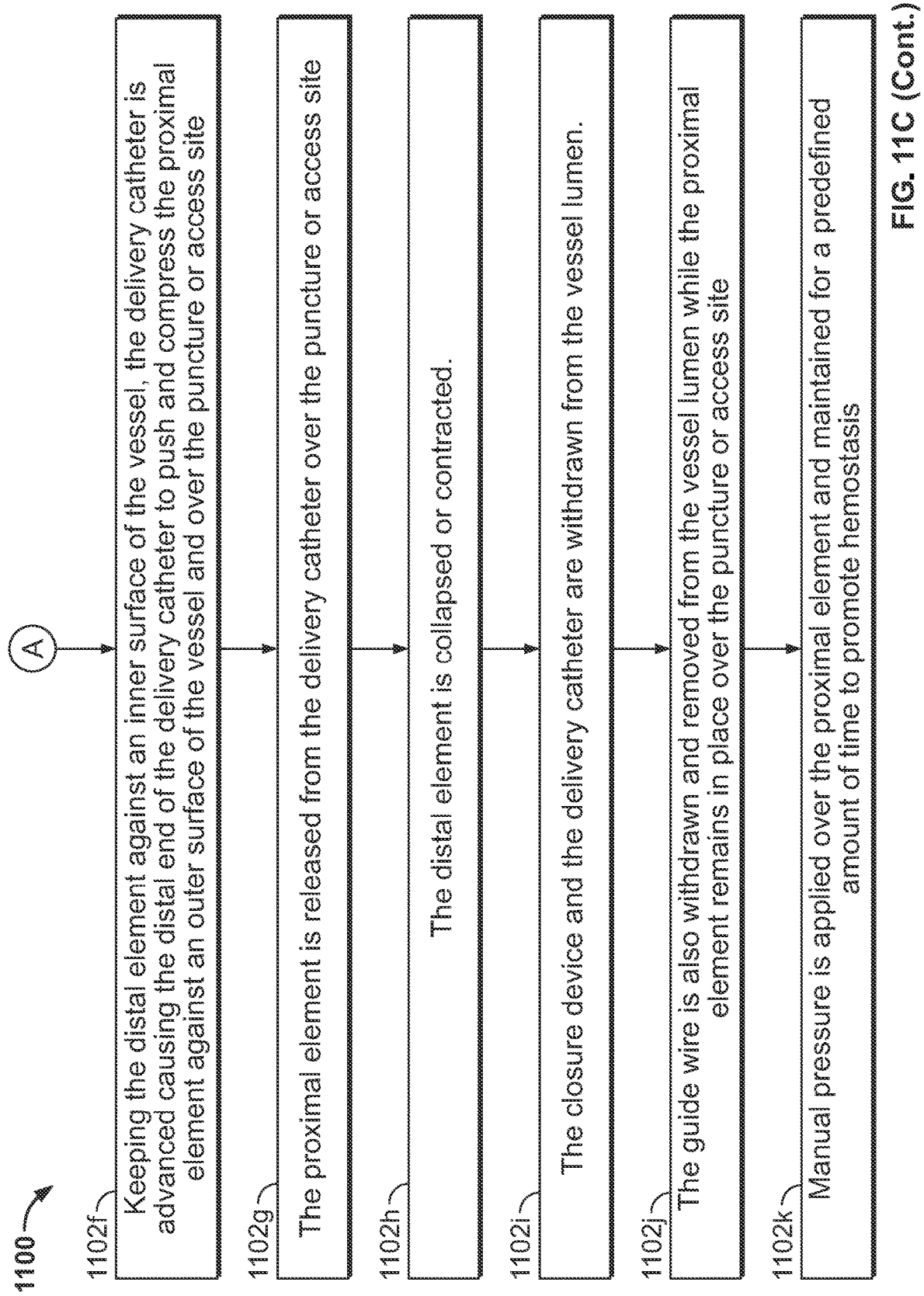

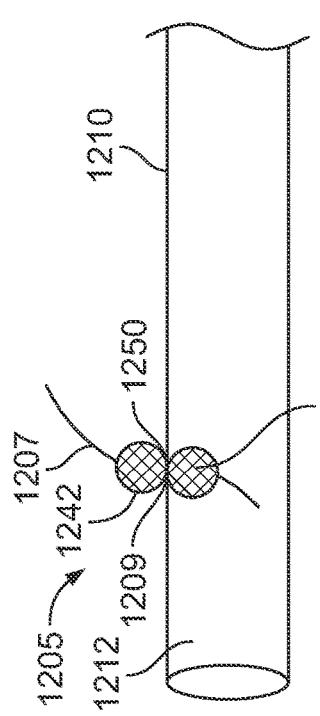

FIG. 12A

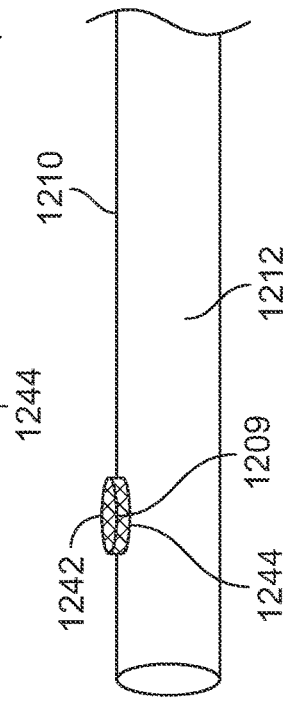

A guide wire is inserted within a sheath and advanced through a puncture or access site of a patient's blood vessel. The sheath is removed so that a distal portion of the guide wire is positioned within a lumen of the vessel while a proximal portion of the guide wire extends outside the vessel A delivery catheter is advanced over the guide wire until blood returns through a proximal end of the delivery catheter. Thereafter, the closure device is inserted and advanced through the delivery catheter so that a waist (point of coupling between proximal and distal elements) is positioned at a level of the puncture or access site.

DEVICES AND METHODS FOR REPAIRING A PATHOLOGICAL CONNECTION BETWEEN TWO ANATOMICAL STRUCTURES

CROSS-REFERENCE

The present application relies on, for priority, U.S. Patent Provisional Application No. 63/215,724, titled "Device and Method of Using the Device for Repairing A Pathological Connection Between Two Anatomical Structures" and filed on Jun. 28, 2021, and U.S. Patent Provisional Application No. 63/215,587, titled "Vascular Closure Devices and Methods of Using Thereof" and filed on Jun. 28, 2021, both of which are herein incorporated by reference in their entirety.

The present application also relies on, for priority, U.S. Patent Provisional Application No. 63/364,168, titled "Clot Removal Methods and Devices with Specialized Clot Removal Elements" and filed on May 4, 2022, and U.S. Patent Provisional Application No. 63/268,094, titled "Methods and Devices for Removing and Filtering Clots to Isolate Blood for Reinfusion into a Patient" and filed on Feb. 16, 2022.

The present application is also a continuation-in-part application of U.S. patent application Ser. No. 17/572,138, titled "Clot Removal Methods and Devices with Multiple Independently Controllable Elements" and filed on Jan. 10, 2022, which is a continuation application of U.S. patent application Ser. No. 17/450,977, of the same title and filed on Oct. 14, 2021.

The present application is also a continuation-in-part application of U.S. patent application Ser. No. 17/572,206, titled "Clot Removal Methods and Devices with Multiple Independently Controllable Elements" and filed on Jan. 10, 2022, which is a continuation application of U.S. patent application Ser. No. 17/450,978, of the same title and filed on Oct. 14, 2021.

Both U.S. patent application Ser. No. 17/450,977 and U.S. patent application Ser. No. 17/450,978 rely on, for priority, the following provisional applications:

U.S. Patent Provisional Application No. 63/260,406, titled "Catheter Based Retrieval Device" and filed on Aug. 19, 2021;

U.S. Patent Provisional Application No. 63/215,724, titled "Device and Method of Using the Device for Repairing A Pathological Connection Between Two Anatomical Structures" and filed on Jun. 28, 2021;

U.S. Patent Provisional Application No. 63/215,579, titled "Hub and Valve Systems for an Aspiration Catheter" and filed on Jun. 28, 2021;

U.S. Patent Provisional Application No. 63/215,573, titled "Aspiration Catheters and Methods of Use Thereof" and filed on Jun. 28, 2021;

U.S. Patent Provisional Application No. 63/215,587, titled "Vascular Closure Devices and Methods of Using Thereof" and filed on Jun. 28, 2021;

U.S. Patent Provisional Application No. 63/215,583, titled "Catheters with Expandable and Collapsible Lumens" and filed on Jun. 28, 2021;

U.S. Patent Provisional Application No. 63/215,565, titled "Catheter Based Retrieval Device" and filed on Jun. 28, 2021; and U.S. Patent Provisional Application No. 63/092,428, titled "Catheter Based Retrieval Device with Proximal Body Having Axial Freedom of Movement" and filed on Oct. 15, 2020.

All of the above-mentioned patents and applications are hereby incorporated by reference in their entirety.

FIELD

The present specification relates generally to medical devices. More particularly, the present specification relates to closure devices configured to occlude a pathologic connection or aperture between first and second anatomical structures or to seal a puncture or access site in a patient's blood vessel.

BACKGROUND

Two walls or septa separate the left and right sides of the heart. The septa can be affected by many defects such as, for example, patent foramen *ovale*, patent ductus arteriosus, atrial septal defects (ASDs), and ventricular septal defects (VSDs). These defects generally correspond to an aperture, flap, or hole in the septum which causes blood to leak between chambers of the heart.

A variety of closure devices have been developed to avoid the risks and discomfort associated with open heart surgery which may otherwise be required to permanently repair the defects in the septa. These closure devices have a small form factor capable of being delivered to and deployed in the heart to seal the defect.

Accordingly, there exists a need for an improved closure device that enables effective closure, sealing or occlusion of a pathological connection or aperture between two anatomical structures. There is also a need for a method of deploying the closure device in a way that allows continued access to the pathological connection or aperture till the closure, sealing or occlusion of the pathological connection or aperture is confirmed.

During cardiovascular and related procedures, at least one catheter is inserted through a puncture or hole to access an artery, such as the femoral artery, or vein of a patient. The at least one catheter, inserted through the puncture or hole in the patient's blood vessel, is guided to a desired location in order to perform procedures such as angioplasty, plaque removal, angiography and/or infusion of a therapeutic substance.

After completion of the procedure, the at least one catheter is removed from the patient's body. Thereafter, the access puncture or hole needs to be closed to prevent or limit the amount of blood that leaks through the vascular access. This is conventionally enabled by applying localized external pressure over the blood vessel manually and then by applying a pressure bandage, compressive weight, or clamp device.

However, such conventional closure procedures are time consuming and often associated with complications such as hematoma or thromboses. With conventional methods, the rate of postpuncture hemorrhage is high, which causes considerable complications. Conventional closure procedures, particularly those using suture-mediated closure devices, have high rates of failure especially in cases related to common vascular disease such as atherosclerosis and calcification.

Accordingly, there is also a need for improved methods and devices that are suitable for closure of vascular punctures with respect to ease-of-use and that do not suffer from the drawbacks of conventional approaches.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a device for occluding an anatomical passage between a first anatomical structure and a second anatomical structure, the device comprising: a handle; a tip portion physically coupled to the handle through a first member and having a proximal element, a distal element, and a second member extending from the proximal element to the distal element, wherein the proximal element is movable axially along the second member of the tip portion and the distal element is not movable along the second member of the tip portion, and wherein each of the proximal element and the distal element is expandable from a substantially linear configuration to an expanded three-dimensional geometric shape which occupies a greater volume than the substantially linear configuration; a first interface integrated into the handle, wherein, upon manipulating the first interface, the proximal element moves axially along the second member of the tip portion; a second interface integrated into the handle, wherein, upon manipulating the second interface, the tip portion uncouples from the first member and the handle; and a locking device configured to be passed over the first member and proximally attach to the tip portion such that it remains in place after the tip portion uncouples from the first member and the handle.

Optionally, the locking device is a nut configured to be crimped against the proximal element.

Optionally, upon the tip portion uncoupling from the first member and the handle, at least one of the proximal element or the distal element proximal is configured to change from the expanded three-dimensional geometric shape to a second three-dimensional geometric shape and wherein the second three-dimensional geometric shape occupies a smaller volume than the expanded three-dimensional geometric shape. Optionally, the second three-dimensional geometric shape is substantially discoidal and the expanded three-dimensional geometric shape is substantially spherical or elliptical.

Optionally, the first interface and the second interface is a button or slider.

Optionally, the second member comprises corrugated walls configured to collapse when the proximal element is moved distally.

Optionally, the second interface is configured to release the tip portion using at least one of a mechanical, electrolytic or thermal release system.

Optionally, at least one of the proximal element, the distal element and the second member are coated with a hydrogel.

Optionally, the second member is coated with a hydrogel adapted to swell to assist in the occlusion of the anatomical passage.

Optionally, the device further comprises a guide wire, wherein the catheter is configured to be advanced over the guide wire for enabling the tip portion to lie across the anatomical passage.

The present specification also discloses a method of occluding an atrial septal defect, comprising: providing a device, wherein the device comprises: a handle; a tip portion physically coupled to the handle through a first member and having a proximal element, a distal element, and a second member extending from the proximal element to the distal element, wherein only one of the proximal element or distal element is movable axially along the second member of the tip portion with a remaining one of the proximal element or distal element being fixed, and wherein each of the proximal element and the distal element is expandable from a substantially linear configuration to an expanded three-dimensional geometric shape which occupies a greater volume than the substantially linear configuration; a first interface integrated into the handle, wherein, upon manipulating the first interface, the proximal element moves axially along the second member of the tip portion; and a second interface integrated into the handle, wherein, upon manipulating the second interface, the tip portion detaches from the first member and the handle; and advancing a guide wire to position the guide wire across the atrial septal defect into a left atrium; advancing a delivery catheter over the guide wire to position the delivery catheter across the atrial septal defect and into the left atrium; advancing the device over the guide wire and through the delivery catheter to position the tip portion of the device across the atrial septal defect; deploying the proximal element in the right atrium side and the distal element in the left atrium side of the atrial septal defect; positioning the distal element to occlude the atrial septal defect on the left atrial side; using the first interface, moving the proximal element relative to the distal element to occlude the right atrial side of the atrial septal defect; advancing a locking device over the guide wire against the proximal element; and using the second interface, releasing the tip portion from the first member, thereby leaving the proximal element, second member, and distal element in place to occlude the atrial septal defect.

Optionally, the method further comprises removing the guide wire, delivery catheter, and first member after leaving the proximal element, second member, and distal element in place to occlude the atrial septal defect.

Optionally, the method further comprises removing the guide wire, delivery catheter, and first member after confirming occlusion of the atrial septal defect using contrast.

Optionally, advancing the locking device over the guide wire against the proximal element comprises advancing a nut over the guide wire and crimping the nut against the proximal element.

Optionally, positioning the distal element to occlude the atrial septal defect on the left atrial side comprises retracting the delivery catheter into a right atrium.

Optionally, upon releasing the tip portion from the first member, at least one of the proximal element or the distal element proximal is configured to change from the expanded three-dimensional geometric shape to a second three-dimensional geometric shape and wherein the second three-dimensional geometric shape occupies a smaller volume than the expanded three-dimensional geometric shape. Optionally, the second three-dimensional geometric shape is substantially discoidal and the expanded three-dimensional geometric shape is substantially spherical or elliptical.

Optionally, the second member comprises corrugated walls configured to collapse when the proximal element is moved distally.

Optionally, the second interface is configured to release the tip portion using at least one of a mechanical, electrolytic or thermal release system.

Optionally, at least one of the proximal element, the distal element and the second member are coated with a hydrogel adapted to swell to assist in the occlusion of the atrial septal defect.

In some embodiments, the present specification discloses a device for occluding a pathologic connection between first and second anatomical structures, the device comprising: a tip portion having a proximal element connected to a distal element through an isthmus, wherein the proximal element is movable axially along the tip portion and the distal element is fixed, and wherein the proximal and distal elements have a first 3D geometric shape; and a handle connected to a proximal end of the tip portion through a shaft, wherein the tip portion is positioned across the pathologic connection so that the proximal element occludes a first side of the pathologic connection and the distal element occludes a second side of the pathologic connection, wherein a nut is crimped against the proximal element, and wherein the tip portion is released at the occluded pathologic connection.

Optionally, the proximal and distal elements have a second 3D geometric shape when occluding the pathologic connection.

Optionally, the second 3D geometric shape is substantially discoid.

Optionally, the first 3D geometric shape is substantially spherical or elliptical.

Optionally, the pathologic connection is an atrial septal defect.

Optionally, the first anatomical structure is a right atrium and the second anatomical structure is a left atrium.

Optionally, the isthmus has corrugated walls that collapse when the proximal element is moved distally towards the distal element for occluding the pathologic connection at the first side.

Optionally, the proximal element, distal element and the isthmus are coated with a hydrogel.

In some embodiments, the device further comprises a first catheter positioned proximate the first anatomical structure; and a guide wire advanced through a second catheter to lie across the pathologic connection, wherein the second catheter is advanced through the first catheter to lie in the first anatomical structure, and wherein the device is advanced over the guide wire for enabling the tip portion to lie across the pathologic connection.

Optionally, a mechanical, electrolytic or thermal release system is used to release the tip portion from the shaft.

In some embodiments, the present specification discloses a method of using a device to occlude an atrial septal defect, wherein the device includes a tip portion having a proximal element connected to a distal element through an isthmus, and wherein a handle is connected to a proximal end of the tip portion through a shaft, the method comprising: positioning a guide catheter in either an inferior vena or in a superior vena cava; advancing a guide wire through a delivery catheter and the guide catheter to position the guide wire across the atrial septal defect into a left atrium; advancing the delivery catheter over the guide wire to position the delivery catheter across the atrial septal defect and into the left atrium; advancing the device over the guide wire and through the delivery catheter to position the device across the atrial septal defect; retracting the delivery catheter into a right atrium; deploying the proximal element in the right atrium side and the distal element in the left atrium side of the atrial septal defect, wherein the proximal and distal elements have a first 3D geometrical shape; pulling the distal element proximally to occlude the atrial septal defect on the left atrial side; moving the proximal element distally to occlude the right atrial side of the atrial septal defect; advancing a nut over the guide wire and crimping the nut against the proximal element; and, releasing the tip portion at the atrial septal defect.

Optionally, the proximal and distal elements have a second 3D geometric shape when occluding the pathologic connection.

Optionally, the second 3D geometric shape is substantially discoid.

Optionally, the first 3D geometric shape is substantially spherical or elliptical.

Optionally, the isthmus has corrugated walls that collapse when the proximal element is moved distally to occlude the right atrial side of the atrial septal defect.

Optionally, a mechanical, electrolytic or thermal release system is used to release the tip portion from the shaft.

In some embodiments, the method further comprises confirming occlusion of the atrial septal defect; and removing the delivery catheter, guide wire and the guide catheter.

Optionally, the occlusion is confirmed by injecting a contrasting agent through the delivery catheter.

Optionally, the proximal element, distal element and the isthmus are coated with a hydrogel.

Optionally, the hydrogel on the isthmus swells to occlude an open space formed when the guide wire is removed.

In some embodiments, the present specification discloses a method for enabling sealing of a puncture site in a patient's vessel using a catheter, wherein the catheter comprises an elongated structure positioned in a lumen of the catheter, a proximal element positioned on the elongated structure and a distal element positioned on the elongated structure, wherein the proximal element and the distal element are each initially in a collapsed state, and a handle coupled to the elongated structure, wherein the handle includes at least one actuation mechanism to expand or collapse the distal element the method comprising: advancing the elongated structure so that the distal element is positioned within a lumen of the vessel; positioning the proximal element outside the vessel; manipulating the at least one actuation mechanism to expand the distal element; positioning the expanded distal element against an inner wall of the puncture site; exposing the proximal element out of the delivery catheter; and positioning the proximal element against an outer surface of the vessel and over the puncture site.

Optionally, the proximal element is released in the compressed state over the puncture site.

Optionally, the at least one actuation mechanism is manipulated to collapse the distal element while the proximal element remains over the puncture site in a compressed state.

Optionally, the catheter is retracted from the vessel while the proximal element remains over the puncture site in the compressed state.

Optionally, the proximal element comprises a plug of poly lactic-co-glycolic acid that is spray coated and impregnated with Genipin.

Optionally, the distal element comprises a tightly woven mesh of Nitinol.

Optionally, the distal element comprises poly lactic-co-glycolic acid.

Optionally, the distal element assumes a three-dimensional geometric shape when expanded, and wherein the three-dimensional geometric shape is substantially spherically shaped, elliptically shaped, umbrella shaped or chalice shaped.

Optionally, the proximal element expands when exposed from the delivery catheter.

In some embodiments, the present specification discloses a method of using a device to seal a puncture site in a patient's blood vessel, the device including a tip having proximal and distal elements in collapsed states, and a handle coupled to the tip through a plurality of telescoping tubes, wherein the handle includes at least one knob to expand or collapse the distal element, the method comprising: positioning a guide wire across the puncture site so that a distal portion of the guide wire lies within a lumen of the vessel and a proximal portion extends outside the vessel; advancing a delivery catheter over the guide wire so that a distal end of the delivery catheter lies within the lumen; advancing the device through the delivery catheter so that the distal element is positioned within the lumen while the proximal and distal elements are covered within the delivery catheter; withdrawing the delivery catheter to expose the distal element without exposing the proximal element; expanding the distal element within the lumen; using the handle to retract the device until resistance is felt due the expanded distal element pressing against an inner surface of the vessel at the puncture site; withdrawing the delivery catheter further to expose the proximal element, wherein said exposing causes the proximal element to expand; advancing the distal end of the delivery catheter to push and compress the proximal element against an outer surface of the vessel and over the puncture site; releasing the compressed proximal element over the puncture site; collapsing the distal element; withdrawing and removing the device from the delivery catheter; withdrawing and removing the delivery catheter from the vessel; and withdrawing and removing the guide wire from the vessel.

Optionally, the at least one knob is actuated in a first direction to expand the distal element, and wherein the at least one knob is actuated in a second direction opposite to the first direction to collapse the distal element.

Optionally, the proximal element is a plug of poly lactic-co-glycolic acid that is spray coated and impregnated with Genipin.

Optionally, the distal element is a tightly woven mesh of Nitinol.

Optionally, the distal element is of poly lactic-co-glycolic acid.

Optionally, the distal element assumes a three-dimensional geometric shape when expanded, and wherein the three-dimensional geometric shape is substantially spherical, elliptical, umbrella or chalice.

In some embodiments, the present specification discloses a device for enabling sealing of a puncture site in a patient's blood vessel, the device comprising: a tip having proximal and distal elements, said proximal and distal elements being in collapsed states, wherein a distal point of the proximal element and a proximal point of the distal element are coupled to form a waist region between the proximal and distal elements; and a handle coupled to the tip through a plurality of telescoping tubes, wherein the handle includes at least one knob to expand or collapse the proximal and distal elements, wherein the device is advanced through a delivery catheter so that the waist is positioned at a level of the puncture site, said delivery catheter being advanced over a guide wire so that a distal end of the delivery catheter lies within a lumen of the vessel and said guide wire being positioned across the puncture site so that a distal portion of the guide wire lies within the lumen while a proximal portion extends outside the vessel, wherein the at least one knob is actuated to expand the proximal and distal elements and the handle is pulled so that the expanded distal element presses against an inner wall of the puncture site, wherein the at least one knob is actuated to collapse the distal element, and wherein the delivery catheter is advanced causing the distal end of the delivery catheter to push and compress the proximal element against an outer surface of the vessel and over the puncture site.

Optionally, the waist is positioned at the level of the puncture site, the distal element is positioned within the lumen and the proximal element is positioned outside the lumen over the puncture site, and wherein the proximal and distal elements are in collapsed states.

Optionally, the proximal and distal elements are released in the compressed state over the puncture site.

Optionally, the at least one knob is actuated in a first direction to expand the proximal and distal elements, and wherein the at least one knob is actuated in a second direction opposite to the first direction to collapse the distal element.

Optionally, the delivery catheter and the guide wire are retracted one after another from the vessel while the proximal and distal elements remain over the puncture site in the compressed state.

Optionally, each of the proximal and distal elements is of poly lactic-co-glycolic acid that is spray coated and impregnated with Genipin.

Optionally, each of the proximal and distal elements is a tightly woven mesh of Nitinol.

Optionally, the proximal and distal elements assume a three-dimensional geometric shape when expanded, and wherein the three-dimensional geometric shape is substantially spherical, elliptical, umbrella or chalice.

In some embodiments, the present specification discloses a method of using a device to seal a puncture site in a patient's blood vessel, the device including a tip having proximal and distal elements in collapsed states, and a handle coupled to the tip through a plurality of telescoping tubes, wherein a distal point of the proximal element and a proximal point of the distal element are coupled to form a waist region between the proximal and distal elements, and wherein the handle includes at least one knob to expand or collapse the proximal and distal elements, the method comprising: positioning a guide wire across the puncture site so that a distal portion of the guide wire lies within a lumen of the vessel and a proximal portion extends outside the vessel; advancing a delivery catheter over the guide wire so that a distal end of the delivery catheter lies within the lumen; advancing the device through the delivery catheter so that the waist region is positioned at a level of the puncture site while the proximal and distal elements are covered within the delivery catheter; withdrawing the delivery catheter to expose the proximal and distal elements; expanding the proximal and distal elements, wherein the expanded proximal element is positioned outside the vessel and over the puncture site while the distal element is positioned within the lumen; using the handle to retract the device until resistance is felt due the expanded distal element pressing against an inner surface of the vessel at the puncture site; compressing the distal element against an inner surface of the puncture site, wherein the distal element is compressed into a discoid shape; advancing the distal end of the delivery catheter to push and compress the proximal element against an outer surface of the vessel and over the puncture site, wherein the proximal element is compressed into a discoid shape; releasing the compressed proximal and distal elements at the puncture site; withdrawing and removing the device from the delivery catheter; withdrawing and removing the delivery catheter from the vessel; and withdrawing and removing the guide wire from the vessel.

Optionally, each of the proximal and distal elements is a tightly woven mesh of Nitinol.

Optionally, the proximal element is a tightly woven mesh of Nitinol and the distal element is of poly lactic-co-glycolic acid.

Optionally, each of the proximal and distal elements assumes a three-dimensional geometric shape when expanded, and wherein the three-dimensional geometric shape is substantially spherical.

In some embodiments, the present specification discloses a device for enabling sealing of a puncture site in a patient's blood vessel, the device comprising: a tip having proximal and distal elements, said proximal and distal elements being in collapsed states, wherein the proximal element has a plurality of downward curving barbs that protrude from a circumference of the proximal element; and a handle coupled to the tip through a plurality of telescoping tubes, wherein the handle includes at least one knob to expand or collapse the distal element, wherein the device is advanced through a delivery catheter so that the distal element is positioned within a lumen of the vessel, said delivery catheter being advanced over a guide wire so that a distal end of the delivery catheter lies within a lumen of the vessel and said guide wire being positioned across the puncture site so that a distal portion of the guide wire lies within the lumen while a proximal portion extends outside the vessel, wherein the at least one knob is actuated to expand the distal element and the handle pulled so that the expanded distal element presses against an inner wall of the puncture site, wherein the delivery catheter is retracted to expose the proximal element and then advanced causing the distal end of the delivery catheter to push and compress the proximal element against an outer surface of the vessel and over the puncture site, said pushing and compressing causing the plurality of barbs to be driven into the adventitia around the puncture site, and wherein the compressed proximal element is retracted away from the vessel to pull the plurality of barbs embedded into the adventitia and seal the puncture site.

Optionally, the proximal element is released over the puncture site after the puncture site is sealed.

Optionally, the at least one knob is actuated to collapse the distal element while the proximal element remains over the puncture site in the compressed state.

Optionally, the device, the delivery catheter and the guide wire are retracted one after another from the vessel while the proximal element remains over the puncture site in the compressed state.

Optionally, each of the proximal and distal elements is a tightly woven mesh of Nitinol.

Optionally, the proximal element is a tightly woven mesh of Nitinol and wherein the distal element is of poly lactic-co-glycolic acid.

Optionally, the distal element assumes a three-dimensional geometric shape when expanded, and wherein the three-dimensional geometric shape is substantially spherical, elliptical, umbrella or chalice.

Optionally, the proximal element assumes a three-dimensional geometric shape when expanded, and wherein the three-dimensional geometric shape is substantially spherical.

Optionally, the proximal element expands when exposed from the delivery catheter.

Optionally, the compressed proximal element has a discoid shape.

Optionally, the compressed proximal element is oriented substantially vertically over the vessel when retracted away from the vessel.

Optionally, the circumference is positioned at a predefined distance below a diameter of the proximal element when said proximal element is in an expanded state.

In some embodiments, the present specification discloses a method of using a device to seal a puncture site in a patient's blood vessel, the device including a tip having proximal and distal elements in collapsed states, and a handle coupled to the tip through a plurality of telescoping tubes, wherein the proximal element has a plurality of downward curving barbs that protrude from a circumference of the proximal element, and wherein the handle includes at least one knob to expand or collapse the distal element, the method comprising: positioning a guide wire across the puncture site so that a distal portion of the guide wire lies within a lumen of the vessel and a proximal portion extends outside the vessel; advancing a delivery catheter over the guide wire so that a distal end of the delivery catheter lies within the lumen; advancing the device through the delivery catheter so that the distal element is positioned within the lumen while the proximal and distal elements are covered within the delivery catheter; withdrawing the delivery catheter to expose the distal element without exposing the proximal element; expanding the distal element within the lumen; using the handle to retract the device until resistance is felt due the expanded distal element pressing against an inner surface of the vessel at the puncture site; withdrawing the delivery catheter further to expose the proximal element, wherein said exposing causes the proximal element to expand; advancing the distal end of the delivery catheter to push and compress the proximal element against an outer surface of the vessel and over the puncture site, wherein said pushing and compressing causes the plurality of barbs to be driven into the adventitia around the puncture site; retracting the compressed proximal element away from the vessel thereby pulling the plurality of barbs close together and sealing the puncture site; releasing the compressed proximal element over the puncture site; collapsing the distal element; withdrawing and removing the device from the delivery catheter; withdrawing and removing the delivery catheter from the vessel; and withdrawing and removing the guide wire from the vessel.

Optionally, the at least one knob is actuated in a first direction to expand the distal element, and wherein the at least one knob is actuated in a second direction opposite to the first direction to collapse the distal element.

Optionally, each of the proximal and distal elements is a tightly woven mesh of Nitinol.

Optionally, the proximal element is a tightly woven mesh of Nitinol, and wherein the distal element is of poly lactic-co-glycolic acid.

Optionally, the distal element assumes a three-dimensional geometric shape when expanded, and wherein the three-dimensional geometric shape is substantially spherical, elliptical, umbrella or chalice.

Optionally, the proximal element assumes a three-dimensional geometric shape when expanded, and wherein the three-dimensional geometric shape is substantially spherical.

Optionally, the compressed proximal element has a discoid shape.

Optionally, the compressed proximal element is oriented substantially vertically over the vessel when retracted away from the vessel.

Optionally, the circumference is positioned at a predefined distance below a diameter of the proximal element when said proximal element is in an expanded state.

The aforementioned and other embodiments of the present specification shall be described in greater depth in the drawings and detailed description provided below.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 10C illustrates a delivery catheter advanced over the guide wire and positioned across the ASD, in accordance with some embodiments of the present specification;

FIG. 10D illustrates the closure device positioned across the ASD, in accordance with some embodiments of the present specification;

FIG. 10G illustrates the distal element covering and occluding the ASD on the left atrial side while the proximal element is positioned on the right atrial side of the ASD, in accordance with some embodiments of the present specification;

FIG. 10H illustrates the proximal element covering or occluding the ASD on the right atrial side and the distal element covering or occluding the ASD on the left atrial side, in accordance with some embodiments of the present specification;

FIG. 10I illustrates a locking nut being advanced over the guide wire, in accordance with some embodiments of the present specification; and FIG. 10J illustrates a tip portion of the closure device released at the ASD, in accordance with some embodiments of the present specification.

FIG. 12A illustrates a closure device being used for performing a vascular closure procedure, in accordance with some embodiments of the present specification;

DETAILED DESCRIPTION

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise", "include", "have", "contain", and forms thereof, are not necessarily limited to members in a list with which the words may be associated. Thus, they are intended to be equivalent in meaning and be openended in that an item or items following any one of these words is not meant to be an exhaustive listing of such item or items, or meant to be limited to only the listed item or items. It should be noted herein that any feature or component described in association with a specific embodiment may be used and implemented with any other embodiment unless clearly indicated otherwise.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred, systems and methods are now described.

The term "clot", "occlusion", "blockage", or "thrombus" shall each be used to refer to material in a patient's veins or arteries that is blocking the flow of blood or material in any of a patient's anatomy that is blocking the flow of any fluid, such as urine.

It should be appreciated that each of the embodiments disclosed herein may be used for occluding a pathologic connection between first and second anatomical structures. For example, the embodiments disclosed herein may be used for septal heart repairs in which a catheter is manipulated to the patient's heart in order to permanently place two connected patches in a hole to cover both the left and right atrial sides.

Figure 1:
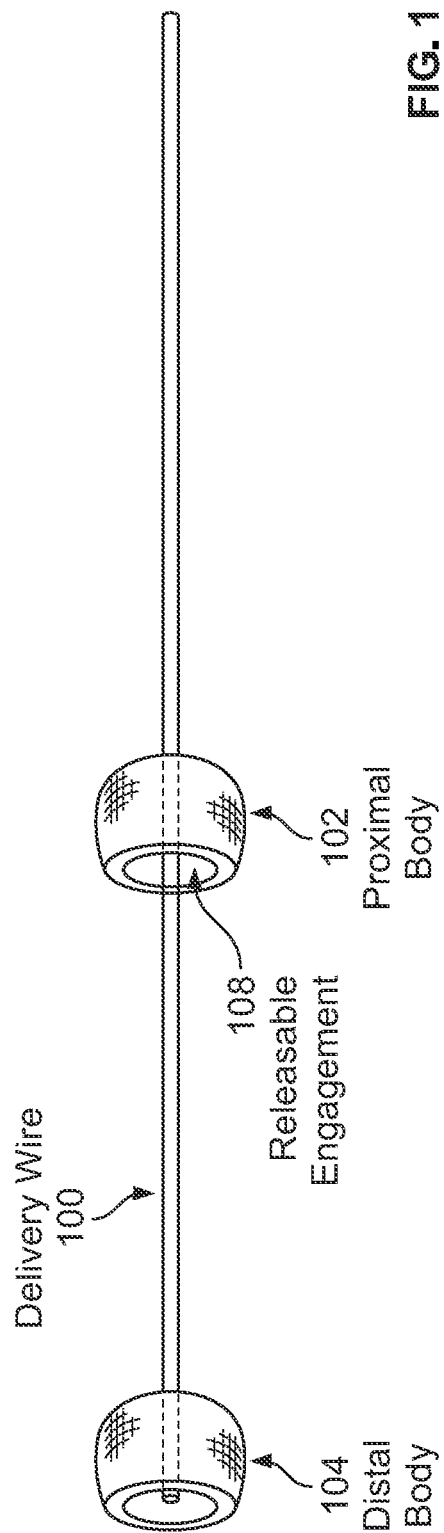
FIG. 1 illustrates a deployment stage of an embodiment of a retrieval device, showing proximal and distal bodies deployed on a delivery wire.

FIG. 1 depicts a deployed retrieval device with a distal body 104, which in this embodiment is a body mounted to the delivery wire 100 such that it remains in a fixed position. Referring to all embodiments disclosed herein, it should be noted that prior to deployment of the delivery wire 100, a guide wire may be used to position any element of the system disclosed herein, including a delivery catheter 202, guide catheter 204, and delivery wire 100 into the preferred position within a vessel or other interior. The "bodies" referred to herein may be a mesh, and they may be made of nitinol or other suitable expandable biocompatible material. The mesh construct of the distal 104 and proximal 102 bodies may reduce the risk of distal embolization of portions of a clot since the mesh construct may capture embolic material within its interstices. The distal body 104 may, in embodiments, have differently-sized mesh or may comprise a selectively permeable material, or it may be non-permeable. A proximal body 102 is also shown. The proximal body 102 is mounted to the delivery wire 100 and is temporarily affixed thereto such that it remains in a fixed position. The temporary affixed aspect referred to above is releasable such that upon release the proximal body 102 may move along the wire, which is referred to herein as "axial movement" along the wire, while remaining engaged to the wire 100. This aspect is referred to as being in "releasable engagement" or being "releasably engaged" to the delivery wire 100. Such releasable engagement may be achieved, for example, by using breakable connection 108, which in embodiments, may be an electrolytically or heat removable/disconnectable connection or mechanical connection that can be selectively disconnected by the clinician. In the case of an electrolytically or heat removable/disconnectable connection, for example, the clinician may apply a current to the connection, (in embodiments via the wire which may be conductive) wherein the electrical current breaks or melts the connection. The connection may include, without limitation, a breakable connection 108, linking a proximal body 102 to the delivery wire 100, that may be eroded and/or disintegrated through the application of electrical current. The breakable connection 108 may be preloaded onto the retrieval device in order to secure the proximal body 102 in a preferred location and/or configuration. The breakable connection may have a plurality of shapes and designs, including but not limited to a straight post extending from the delivery wire 100 to the proximal 102 or other body, a loop configuration of the breakable connection passing through the material of the proximal 102 or other body, and/or a "nail" configuration in which a straight post extends from the delivery wire to the proximal 102 or other body, wherein the post has an enlarged end, or nail head, within the body that may be eroded by the application of electric current to release the body. Embodiments of the present invention include a proximal 102 or other body that may be secured to the delivery wire 100 using more than one breakable connection 108. In an example, a proximal body 102 may be secured with multiple breakable connections, each having a different length and a different release threshold, allowing the breakable connections to be sequentially released. In embodiments, more than one proximal body may be secured to the delivery wire 100 using a breakable connection 108. Melting of a breakable connection may be caused by the application of electrical current, fluid, and/or chemical compounds. Melting may occur in a physical member that is used to secure the proximal or distal body and/or may occur within an adhesive that binds the physical member to the proximal, and/or the delivery wire 100. Breakable connection techniques and methods, including but not limited to those shown in U.S. Pat. Nos. 5,683,451, 5,855,578, 6,245,076, 8,273,116. and U.S. patent applications 20070100414A1, 20090062726A1, and 20100268251A1, may be used to release a proximal body and/or distal body, as described herein. In the case of a mechanically breakable connection, the breakable connection 108 may be made of a suture, brace, thread or other material that is able to be broken upon application of force to the breakable connection 108. In embodiments, the distal motion of a catheter, such as the delivery catheter, with a force above the threshold holding force of the breakable connection 108 may cause the connection 108 to break or release, thus allowing the body 102 to move along the wire in the manners described herein. The "bodies" referred to herein may be of various geometric shapes including a disc or sphere. In embodiments, the distal body 104 and/or proximal body 102 may be an inflatable device, including but not limited to an inflatable balloon. In embodiments, a retrieval device, as described herein, may include a distal body 104 and a proximal body 102 made of differing materials, for example a proximal body 102 may be an inflatable balloon and a distal body 104, on the same retrieval device, may be made of a mesh material. In embodiments, by adjusting the manufactured radial force, body diameter, and strength of the bodies, foreign body extraction, as described herein, may also be used for the removal of stones, pulmonary emboli, or some other type of obstruction. In embodiments, a proximal and/or distal body may have variable radial force, or stiffness across subregions of the body itself. For example, the upper hemisphere of a spherical body may have a difference radial force characteristic than the lower hemisphere of the body. In embodiments, the proximal and distal bodies may be substantially the same. In other embodiments, the proximal and distal bodies may be heterogeneous, having different compositions and characteristics including, without limitation, shape, size (e.g., thickness, diameter), configuration, pore size (e.g., mesh pore size), coating, or some other differing characteristic. In embodiments, the proximal and/or distal bodies may have anti-platelet, or some other type of, coatings to reduce adhesion and provide a less thrombogenic environment during clinical application. The proximal and/or distal bodies, and any material (e.g., wires) between these bodies, may be coated with control release agents including, but not limited to, thrombolytic agents.

The "delivery wire" 100 referred to herein may be a wire or a hypo tube. The delivery wire 100 may not require a coaxial system of catheters as disclosed herein in embodiments.

The "delivery catheter" 202 referred to herein may be referred to as a microcatheter, and may form a plurality of shape configurations based on the clinical application in which it is used, for example, which type of vessel the delivery catheter is used within, the vessel size, the vessel shape, or some other application characteristic. In embodiments, a delivery wire and/or hypo tube may be used within a microcatheter. For purposes of this disclosure, the microcatheter 202 is commonly called a "delivery catheter", although it should be understood that the terms can be used interchangeably.

Figure 2:
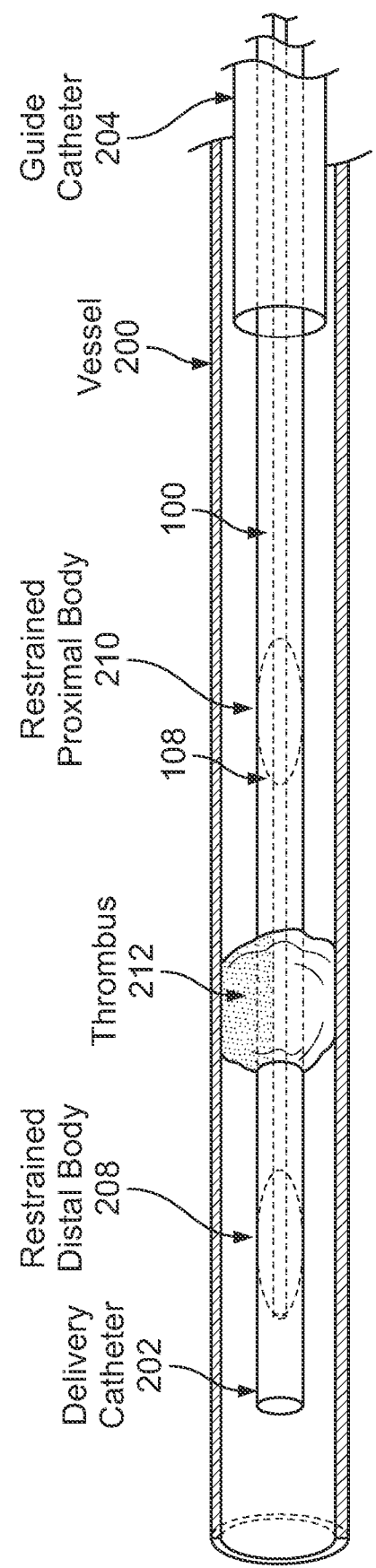
FIG. 2 illustrates the pre-deployment stage of the proximal and distal bodies, where the proximal and distal bodies are restrained or unexpanded.

Referring to FIG. 2, prior to deployment of the distal 208 and proximal 210 bodies (which are shown as being restrained or in their unexpanded form and thus having different reference numerals from the FIGS. 1, and 3-5) the delivery catheter 202 surrounds the delivery wire and restrains both bodies 208, 210. In embodiments, a guide catheter 204 is navigated into place, in embodiments, over a guide wire, said guide wire in some embodiments being removed. The delivery catheter 202 may be passed through an object, such as a thrombus or clot 212, the bodies 208, 210 may be released from the delivery catheter 202 either by retracting the delivery catheter 202 or advancing the wire 100, such that expandable bodies are no longer restrained by the delivery catheter 202. The distal body 104 remains fixed to the delivery wire 100, but the proximal body 102 (once released from its releasable engagement) can freely move along its axis and longitudinally along the delivery wire 100 when pushed by the delivery catheter 202. Also, the delivery wire 100 "pushing" the body (210 or 102 once expanded) must be understood as relative pushing. That is, the retraction of the delivery wire 100 while the delivery catheter 202 is kept in place may serve to move the proximal body 102 axially along the wire. The term "pushing" as is used herein will refer to both forms of movement mentioned above. Once the proximal and distal bodies are positioned adjacent to both sides of the clot (which has been referred to herein as "surrounded" or "surrounding" the clot) by movement of the proximal body 102, the clot may be removed by retrieving the device from the cavity and pulling the clot free. The terms "clot," "thrombus," "occlusion," "occlusive substance" and "foreign body" may be used interchangeably herein.

In embodiments, the freedom of movement of the proximal body 102 on the delivery wire 100 axially may allow for the compression of the occlusive substance and obviate the need for premeasuring or estimating the required distance between the distal and proximal bodies prior to entering the vessel 200; sizing may take place in situ within the vessel 200 upon the interventionist encountering it.

In embodiments of the present disclosure, the retrieval device may consist of a distal body 104 and a proximal body 102, each of which in embodiments may be collapsible geometric forms. Although the distal and proximal bodies are presented for diagrammatic purposes as spherical, the distal and proximal bodies may also be other geometric forms such as a disc, cone, oblong-shaped form, etc. As mentioned above, the distal and proximal bodies may be a mesh in structure. The mesh cell size may be manufactured to have different sizes based on factors such as the expected properties of the target foreign matter to be removed, such as the density of the matter. The distal body 104 is mounted on a delivery wire 100 such that it remains fixed. In embodiments, the mounting of the proximal body 102 occurs by running the wire through one of the mesh opening. In other embodiments, the proximal body 102 itself may have an opening through which the wire may pass. In either case of mounting the proximal body 102, the body is able to slide along the wire in an axial direction along the wire. This may be referred to herein as "slidably mounted". In some embodiments, the distal body 104 may be slidably mounted in the way described above. As described above, the proximal body may be detachable (thus releasably engaged) using mechanical, electrolytic or some other type of control release format. In embodiments, the proximal body 102 will be slidable along the wire one released while the distal body 104 remains fixed. In other embodiments, both the proximal and distal bodies may be releasably engaged and thus slidable or movable along the delivery wire 100. Still in other embodiments, the proximal body 102 may be comprised of multiple bodies, and the distal body 104 may be comprised of multiple bodies. The mesh material of the distal and proximal bodies may have advantages over other material types, including but not limited to inflatable balloons. Inflatable material may be susceptible to rupture, such as that caused by over inflation. The clinical setting may also be associated with complications related to the use of inflatable balloons within a lumen. For example, a calcified thrombus may increase the risk of balloon rupture. In another example, if an occlusion itself includes metallic material, this may also increase the risk of rupture or other malfunction of an inflatable balloon. Rupture of a balloon may in turn increase the risk of an air embolus forming within the vessel or cavity of intervention. In embodiments, the mesh material of the distal and proximal bodies may allow for the bodies to expand upon release to the diameter and configuration of the cavity in which it is placed, such as a vessel 200 in which a thrombus 212 is located. Such meshes may be made of a shape memory substance such as nitinol. For example, a body made of nitinol mesh may expand to a first dimension outside of a vessel 200 or catheter, but may be designed to expand to a continuum of smaller dimensions than the first dimensions corresponding to different lumen sizes. In this way the bodies may fit the unique variations in diameter found in a lumen at the point of release and/or point of placement near an occlusion, such as a thrombus. Mesh material may also allow for improved distal flow during an intervention. The irregularity and/or texture of the expanded mesh material may facilitate the mesh material becoming entangled or otherwise incorporated with a clot or occlusive substance, thereby increasing adhesion of the distal and/or proximal body with the occlusion and facilitating its removal.

Figure 3:
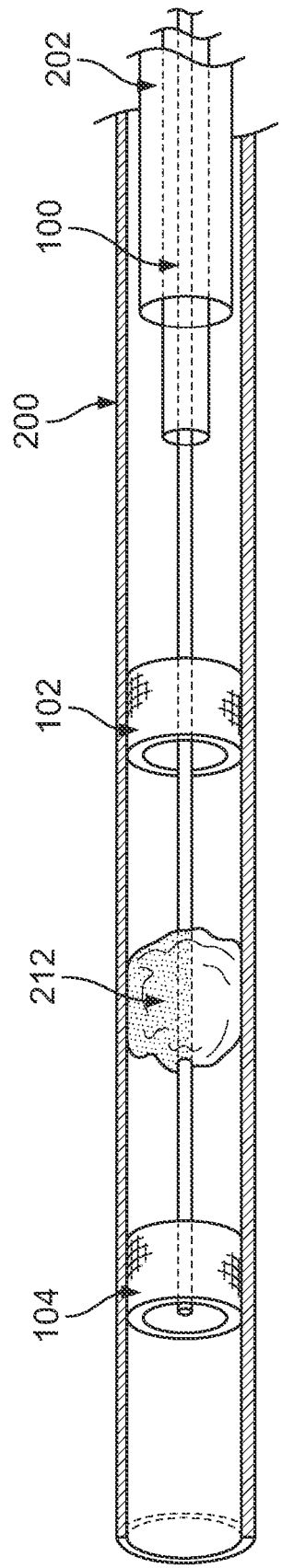
FIG. 3 illustrates the expanded or released position of the proximal and distal bodies from the delivery catheter.
Figure 4:
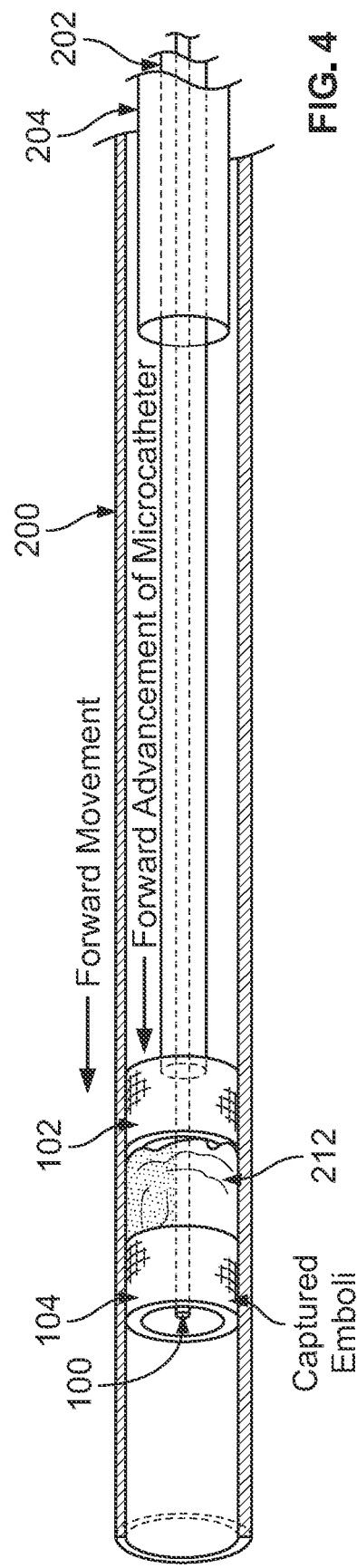
FIG. 4 illustrates advancing the proximal body of the retrieval device axially along the delivery wire to trap and compress a thrombus.
Figure 5:
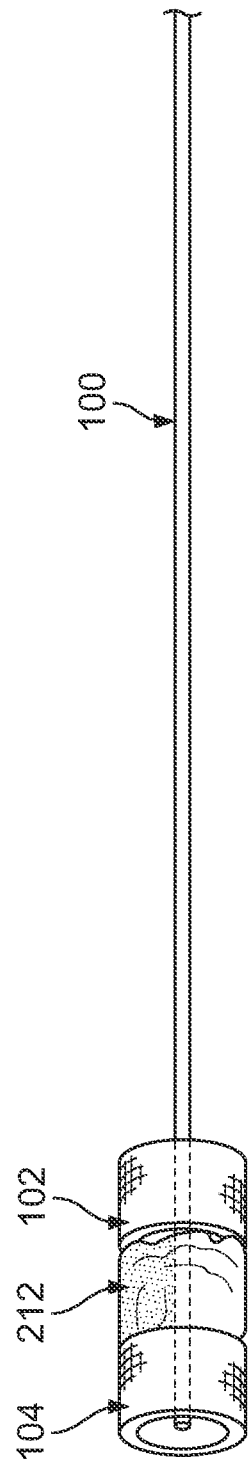
FIG. 5 illustrates the removal of a thrombus using the deployed proximal and distal bodies of an embodiment of the retrieval device.

In embodiments, when the proximal body 102 is released, it may be free to move/slide on its axis along the delivery wire 100 in a longitudinal and/or rotational fashion. Referring to FIG. 3 when the distal body 104 is placed distal to the target thrombus 212 for retrieval and the proximal body 102 is placed proximal to the thrombus 212, the distal and proximal bodies will straddle and contain the thrombus 212 intended for removal from the vessel. The proximal body 102 may now be advanced in the direction of the thrombus 212 in a variety of mechanical fashions. As shown in FIG. 4, a coaxially placed microcatheter, also referred to herein as a "delivery catheter" 202, may be pushed forward (once the proximal body is released) and used to physically advance the proximal body 102 to ultimately capture and compress the thrombus 212. Alternatively, the delivery catheter 202 may be used to hold the proximal body 102 in a fixed position while the delivery wire 100 is withdrawn thus moving the fixed distal body 104 towards the proximal body 102 and ultimately capturing and compressing the thrombus 212. As shown in FIG. 5, once the thrombus 212 is captured/compressed between the distal body 104 and the proximal body 102, the entire retrieval device may be removed from the patient via withdrawal of the delivery wire 100 by, for example, withdrawing the proximal and distal bodies with the compressed material back to, and against, the delivery catheter and then removing the delivery catheter, bodies and compressed material through the guide catheter. Once this is removed, the guide catheter may be withdrawn from the vessel.

The methods, system and apparatus, as described herein, may have a plurality of sizes loaded within a common catheter, and a clinician may self-load, for example, different and/or additional proximal bodies, as described herein, rather than having to fully replace a deployed catheter for a second catheter-based device and system. This may reduce manufacturing costs and improve intervention efficiency.

A Closure Device for Repairing a Pathological Condition Between Two Anatomical Structures The present specification discloses embodiments of a closure device for sealing a pathologic connection or aperture between first and second anatomical structures and methods for using the various embodiments of the closure device. In various embodiments, the closure device includes a tip having a proximal element and a distal element and a handle coupled to the tip through a plurality of telescoping tubes, wherein the handle includes at least one actuator to expand or collapse at least one of the proximal and distal elements, move the proximal and distal elements relative to one another, and release the tip. In some embodiments, the proximal element is a PGLA (poly lactic-co-glycolic acid) plug spray-coated and impregnated with Genipin while the distal element is a tightly woven mesh of Nitinol. In some embodiments, each of the proximal and distal elements is a tightly woven mesh of Nitinol.

In some embodiments, the distal element optionally comprises PGLA, which may or may not be spray-coated and may optionally be impregnated with Genipin. In some embodiments, the PGLA based distal element may be left inside the patient's vessel lumen at the end of a closure procedure. In such embodiments, the PGLA based distal element is adapted to gradually be resorbed or dissolved into the body.

The PGLA/Genipin based proximal element or distal element is a resorbable element that has an ability to crosslink fibrin allele groups thereby making it highly resistant to enzymatic degradation. The crosslinking also occurs between fibrin and surrounding tissues, proteins, in fat, external vessel walls, and muscle. This crosslinking provides thrombus and PGLA stability and reduces the likelihood of movement of the element(s) and potential displacement of the closure device proximal or distal elements.

In various embodiments, the distal element, composed of a tightly woven mesh of elastic material, such as Nitinol, expands within a pathologic connection or aperture between first and second anatomical structures, such as, for example, an arterial septal defect, thereby interrupting the flow of blood between the two anatomical structures and effectively sealing off the connection or aperture. In various embodiments, the closure device enables the sealing of pathologic connection or aperture sites in any anatomic structure such as (but not limited to) cardiac structural defects (patent foramen *ovale*, septal wall defects, atrial appendages), arterio-venous fistulas, enteric fistulas, and organ perforations. It should be appreciated that the distal element may have a surface area defined by a mesh having interlaced wire defining a plurality of spaces or voids. In one embodiment, the total surface area of the voids is a value equal to or within any number ranging from 10% to 90% of the total surface area of the distal element.

Figure 6:
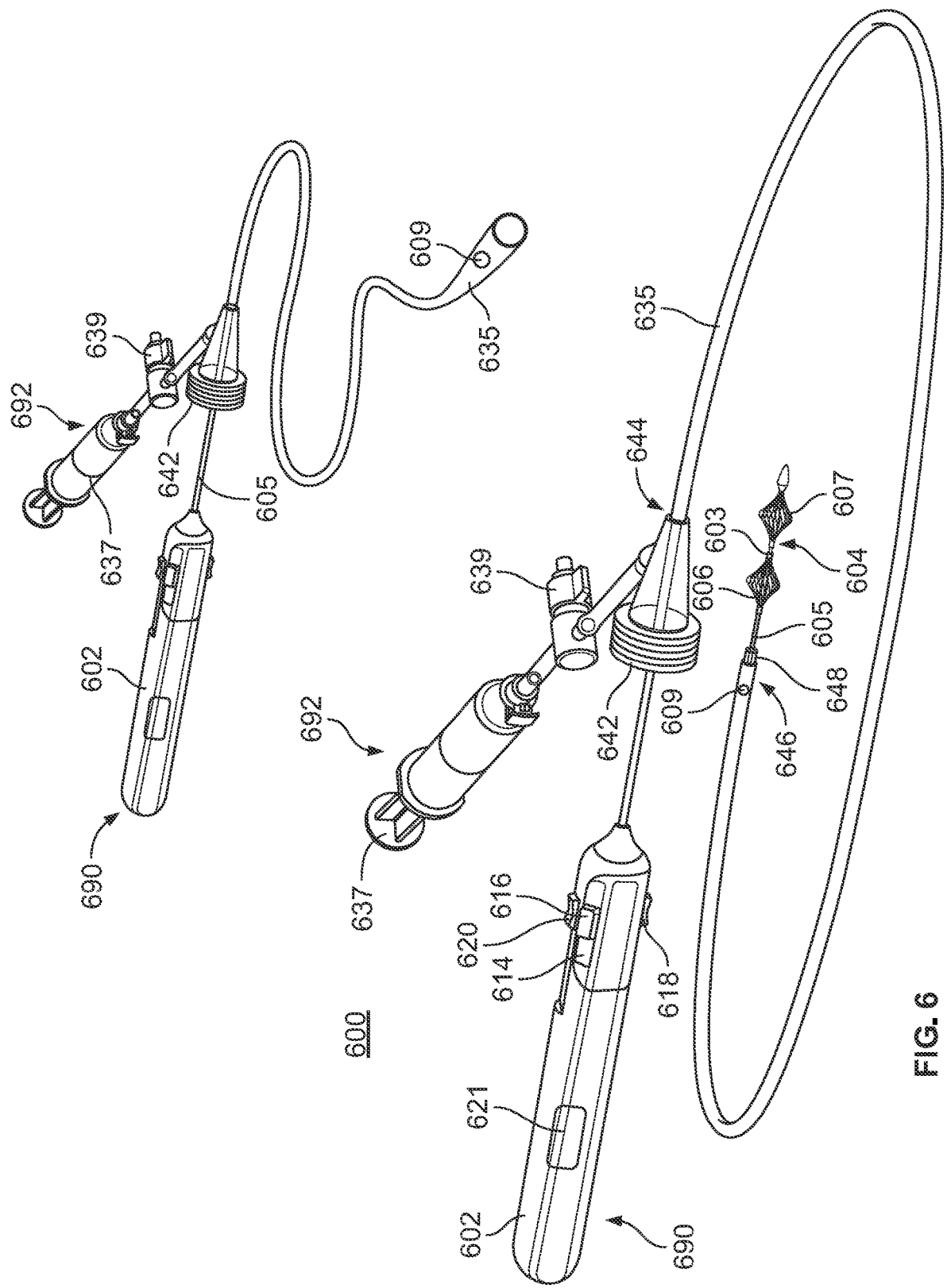
FIG. 6 is a perspective view of a closure device, in accordance with an embodiment of the present specification.

FIG. 6 illustrates a closure device, in accordance with some embodiments of the present specification. Device 600 comprises a first unit 690 that includes a handle 602 coupled to a proximal end of a first member 605, which in embodiments is an elongated or tubular member, having a plurality of telescoping tubes, such as at least four telescoping tubes, wherein a distal end of the elongated first member 605 has a tip portion 604. The handle 602 is configured to steer the tip portion 604 in proximity to a pathologic connection or aperture between first and second anatomical structures. Tip portion 604 includes a proximal element 606 and a distal element 607 connected by a second member 603. In embodiments, the second member is a collapsible isthmus or bridge 603 and is further described in detail with reference to FIGS. 7A and 7B. The handle 602 is further described in detail with reference to FIG. 8. The device 600 further comprises a second unit 692 that includes an aspiration catheter 635 having a suction source such as, for example, a syringe 637, a one-way valve 639 and a port 642, where the port 642 is coupled to a proximal end 644 of the aspiration catheter 635. In one embodiment, the one-way valve 639 is configured to direct suction through the aspiration catheter 635. For use during a procedure, the tip portion 604 is placed into a delivery catheter 648 and thereafter the delivery catheter 648 is inserted into the aspiration catheter 635, and follows through to port 642, so that at least the tip portion 604 projects distally from a distal end 646 of the aspiration catheter 635.

In accordance with aspects of the present specification, the device 600 is configured to enable an operator to single-handedly operate/actuate the handle portion 602 (using interfaces including first, second, third, and fourth physically manipulable interfaces such as, for example, knobs, sliders, buttons or other actuation mechanisms 614, 616, 618 and 620) in order to mechanically expand, contract, or move a members of the distal end, as further discussed subsequently. A first interface integrated onto handle portion 602 enables proximal element 606 to move axially along isthmus or bridge 603. A second interface integrated onto handle portion 602 enables uncoupling of tip portion 604 from the elongated first member 605 and the handle. Third and fourth interfaces integrated onto the handle portion 602 enable transition of the proximal and distal elements from substantially linear configurations into first expanded 3D geometric shapes and then, in some embodiments, into second 3D geometric shapes. In some embodiments, blood may be aspirated by actuating the hub 639.

In one embodiment, the first slider, knob, button, or other actuation mechanism 614, the second slider, knob, button, or other actuation mechanism 618, and the third slider, knob, button, or other actuation mechanism 620 are positioned in an arc around an external surface of the handle 602 such that each of the first, second, and third actuation mechanisms are at the same location, or within 3 inches, axially along the length of the handle.

In accordance with some aspects of the present specification, the first and second units 690, 692 are manufactured as separate standalone units or devices. This is advantageous in that a physician may use the first unit 690 with any third-party aspiration catheter. In some embodiments, the aspiration catheter 635 is available with a plurality of external diameters such as, but not limited to, 12 Fr, 16 Fr, 20 Fr, and 24 Fr (where Fr represents French scale or gauge system). In some embodiments, the syringe 637 has an exemplary, non-limiting, volume of 60 cubic centimeters.

In some embodiments, the closure device 600 is designed for venous and arterial use with a maximum outer diameter of 26 French for the arterial vessels and 29 French for the venous vessels.

During operation of the device 600, the tip portion 604 is inserted into, for example, a blood vessel for performing a closure while the handle portion 602 remains in an operator/user's hands. While in some embodiments, the handle portion 602 includes four interfaces 614, 616, 618, 620 to manipulate the elements at the distal end, in alternate embodiments, fewer than four interfaces or more than four interfaces may be used.

In some embodiments, at least one pressure transducer or sensor 609 (such as, for example, a fiber-optic pressure sensor, electro-mechanical pressure sensor and hydraulic pressure sensor) is positioned at a distal end of aspiration catheter 635. In some embodiments, the at least one pressure transducer or sensor 609 is in the form of an elongated member that is co-extruded into the aspiration catheter 635 so that the elongated member runs along a full length of the aspiration catheter 635. In embodiments, the pressure transducer or sensor 609 is in electrical communication with electronic circuitry located in the handle 602 of the first unit 690. In embodiments, the handle 602 includes a pressure display 621. In various embodiments, the pressure transducer or sensor 609 is configured to sense a pressure change or drop and, in particular, provide the physician with an indication that, as the pathologic connection or aperture is closed, there is an associated change of pressure indicative of the closure.

Figures 7A, 7B:
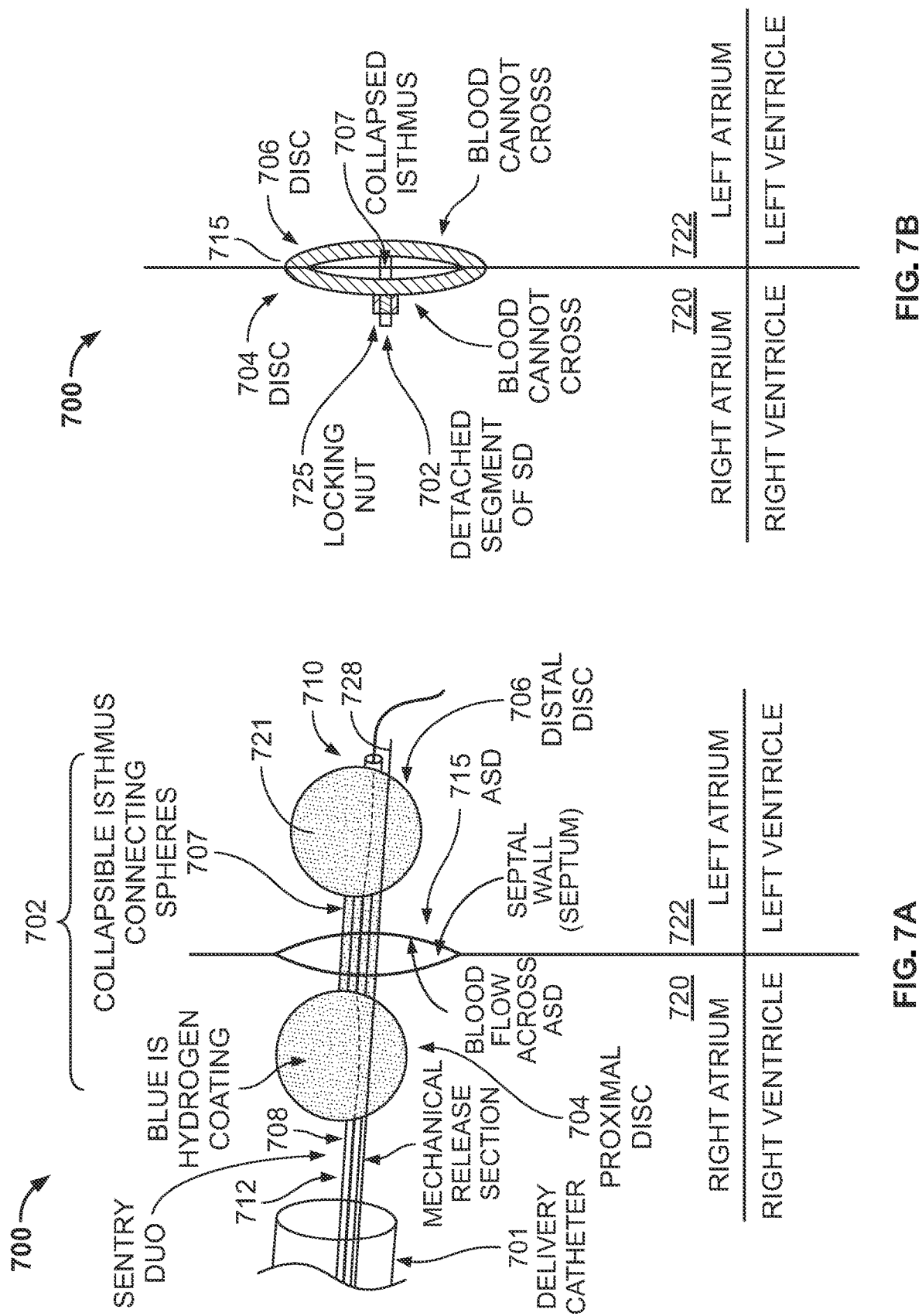
FIG. 7A illustrates a closure device positioned across an atrial septal defect (ASD) in a patient's atria, in accordance with some embodiments of the present specification.
FIG. 7B illustrates the ASD being sealed using the closure device, in accordance with some embodiments of the present specification.

FIG. 7A illustrates a closure device 700 positioned across an atrial septal defect (ASD) in a patient's atria while FIG. 7B illustrates the ASD being sealed using the closure device 700, in accordance with some embodiments of the present specification. As shown in FIG. 7A, the closure device 700 is delivered via a delivery catheter 701 and comprises a tip portion 702 having a proximal element 704 and a distal element 706. The proximal and distal elements 704, 706 are connected by a second member (or collapsible isthmus or bridge) 707. The proximal element 704 is movably attached to a proximal end 708 of the tip portion 702 while the distal element 706 is fixedly coupled to a distal end 710 of the tip portion 702. In some embodiments, proximal element 704 is movable axially along second member (or isthmus or bridge) 707 of the tip portion 702, and distal element 706 is not movable along the second member (or isthmus or bridge) 707. In other words, the distal element 706 is fixed while the proximal element 704 is movable axially along the tip portion 702. In some embodiments, only one of proximal element 704 and distal element 706 is movable along second member (or isthmus or bridge) 707, while the other element (distal or proximal) is fixed such that it is not movable along the second member (or isthmus or bridge) 707. In some embodiments, only proximal element 704 is movable along the second member 707 while distal element 706 is fixed such that it is not movable along the second member 707. In other embodiments, only distal element 706 is movable along the second member 707 while proximal element 704 is fixed such that it is not movable along the second member 707.

Figure 8:
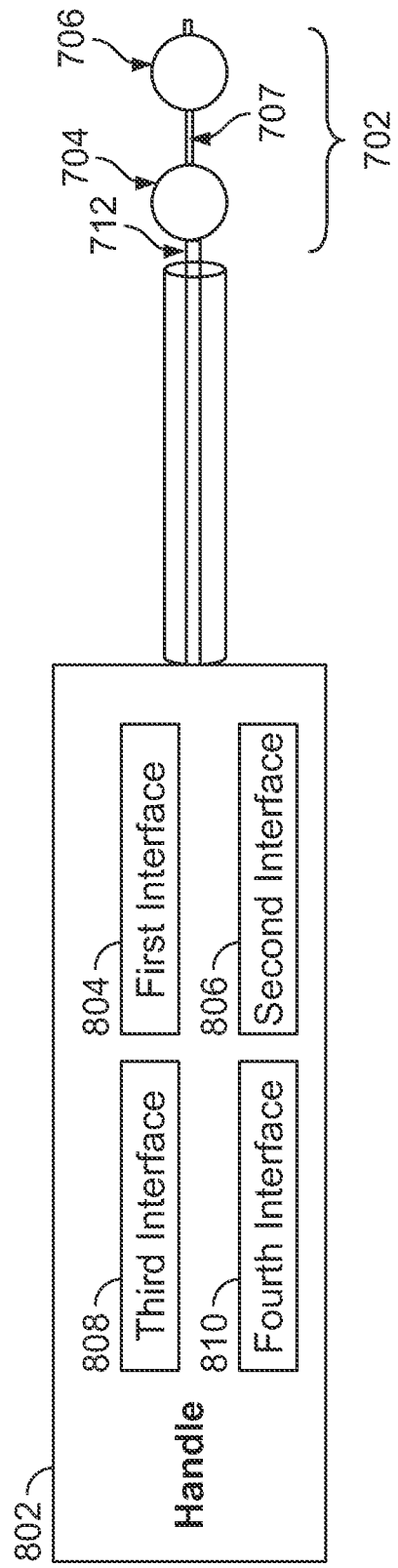
FIG. 8 illustrates an exemplary schematic of a handle used with the closure system in accordance with an embodiment of the present specification.

FIG. 8 illustrates an exemplary schematic of a handle 802 used with the closure system in accordance with an embodiment of the present specification. The tip portion 702 is connected to handle 802 through a first member (or elongated shaft or tubular portion) 712. The handle 802 includes an interface 804 (button or lever) to move the proximal element 704 axially along the tip portion 702 and a interface 806 (second button or lever) to release the tip portion 702, including the proximal element 704, second member 707, and distal element 706, when desired. In embodiments, the handle 802 includes a third interface 808 (button or lever) to change the proximal element 704 from a substantially linear configuration to first expanded three-dimensional (3D) geometric shape and then to a second three-dimensional (3D) geometric shape. In embodiments, the handle 802 includes a fourth interface 810 (button or lever) to change the distal element 706 from a substantially linear configuration to first expanded three-dimensional (3D) geometric shape and then to a second three-dimensional (3D) geometric shape. In various embodiments, the tip portion 702 is released using a mechanical, electrolytic or thermal release system that detaches the tip portion 702 from the first member (proximal shaft or tubular portion) 712.

In some embodiments, the second member (or isthmus or bridge) 707 has corrugated walls which collapse as the proximal element 704 is moved distally towards the distal element 706 using the first button or lever on the handle.

The proximal and distal elements 704, 706 have a substantially linear configuration for delivery during placement of the closure device, a first expanded three dimensional (3D) geometric shape when deployed (as shown in FIG. 7A) and, in some embodiments, a second three dimensional (3D) geometric shape when used to seal or occlude a pathologic connection between two anatomical structures (as shown in FIG. 7B). In embodiments, the first expanded three-dimensional geometric shape occupies a greater volume than the substantially linear configuration. In some embodiments, the second three-dimensional geometric shape occupies a smaller volume than the first expanded three-dimensional geometric shape. In other words, the proximal and distal elements 704, 706 are configured to be in a linear configuration to allow passage through the patient's vasculature during insertion and delivery to the deployment site, and configured to transition to a first expanded 3D geometric shape and, in some embodiments, to a second 3D geometric shape. In some embodiments, the first 3D geometric shape is substantially spherical or elliptical. In some embodiments, the second 3D geometric shape is substantially discoid, quadrilateral or polygonal.

In some embodiments, the tip portion 702 including the proximal element 704, distal element 706 and the second member (or isthmus or bridge) 707 have a hydrogel coating to improve or enhance a watertight closure, sealing or occlusion of a pathologic connection between two anatomical structures such as, for example, atrial septal defect (ASD), gastrointestinal/enteric fistulas, genito/gyneco/urologic fistulas, and arteriovenous fistulas (AVF). The hydrogel swells or expands volumetrically in contact with fluid. The hydrogel serves to increase a surface volume of the closure device across the pathologic connection thereby improving the quality of the fluid closure, seal or occlusion across the pathologic connection.

In various embodiments, the hydrogel is a low molecular weight ethylenically unsaturated macromer or an ethylenically unsaturated monomer. In some embodiments, the macromer polyethylene glycol, propylene glycol, poly(tetramethylene oxide), poly(ethylene glycol) diacrylamide, poly(ethylene glycol) diacrylate, poly(ethylene glycol) di methacrylate, derivatives thereof, or combinations thereof.

In some embodiment, the closure device, further comprises a guide wire 728, wherein the delivery catheter 701 is configured to be advanced over the guide wire 728 for enabling the tip portion to lie across the anatomical passage. In accordance with aspects of the present specification, the guide wire 728 remains across the pathologic connection till closure of the pathologic connection is confirmed. The guide wire is removed from the patient's body once closure is confirmed. In some embodiments, when the guide wire is removed, the hydrogel on the second member (or isthmus or bridge) 707 swells and occludes any open space at the center of the second member (or isthmus or bridge) 707 thus eliminating any blood flow through a small open tunnel (across the pathologic connection) that remains when the guide wire is removed.

It should be appreciated that while the closure device 700 of the present specification can be used to effectively close, seal or occlude any pathologic connection between two anatomical structures, the present specification will now describe, as an exemplary illustration, use of the closure device 700 for effectively closing, sealing or occluding an ASD.

During use, as shown in FIG. 7A, the closure device 700 is deployed to be positioned across an ASD 715 such that the proximal element 704 is positioned in the right atrium 720 and the distal element 706 is positioned in the left atrium 722. At this stage, the proximal and distal elements 704, 706 have the first 3D geometric shape. Thereafter, as shown in FIG. 7B, the distal element 706 is pulled proximally to abut and cover or occlude the ASD 715 on the left atrial side while the proximal element 704 is moved distally (causing the second member or isthmus or bridge 707 to collapse) till the proximal element 706 covers or occludes the ASD 715 on the right atrial side. Eventually, the proximal and distal elements 704, 706 press against the opposing sides of the ASD 715 thereby sealing or occluding the ASD 715 in between while transitioning to the second 3D geometric shape. A locking device 725, in some embodiments, in the form of a nut, is crimped against the proximal element 704 in order to keep the proximal and distal elements 704, 706 opposed and covering the ASD 715 and securing the seal. The collapsed tip portion 702, with the proximal and distal elements 704, 706 in the second 3D geometric shape, is then released at the site 715 of the seal or closure.

In some embodiments, the closure device is used to close a septal defect having a diameter of at least 10 mm. In some embodiments, for sealing the septal defect, the proximal element 606 and distal element 607, when in the first expanded 3D geometric shape and in the second 3D geometric shape, each have a diameter in a range of 5 mm to 20 mm. The second member 603 is configured to collapse or retract toward 0 mm as the proximal element 606 and distal element 607 are drawn together to close the opening between the two anatomical structures (atria). In embodiments, the second member is configured to span the thickness of an atrial septum before the proximal element and distal element are opposed to one another, thus sealing the hole. In embodiments, for closing a septal defect, the length of the second member ranges from 0.1 mm to 20 mm. In some embodiments, for closing a hole in a patient's blood vessel, the length of the second member is 15 mm.

A Method of Using the Closure Device

Figure 9:
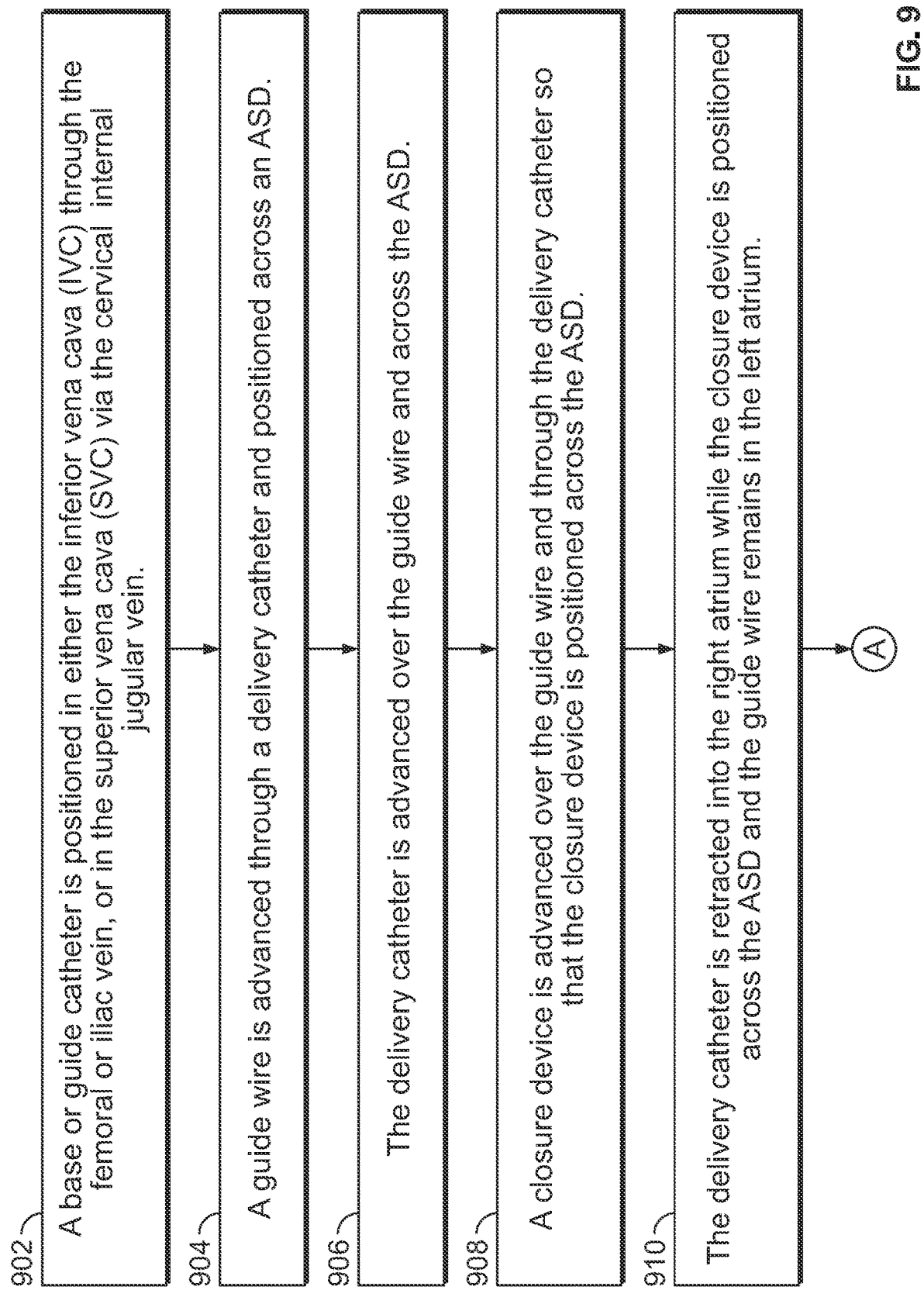
FIG. 9 is a flowchart of a plurality of exemplary steps of a method of using the closure device to close, seal or occlude an atrial septal defect (ASD), in accordance with some embodiments of the present specification.
Figure 10B:
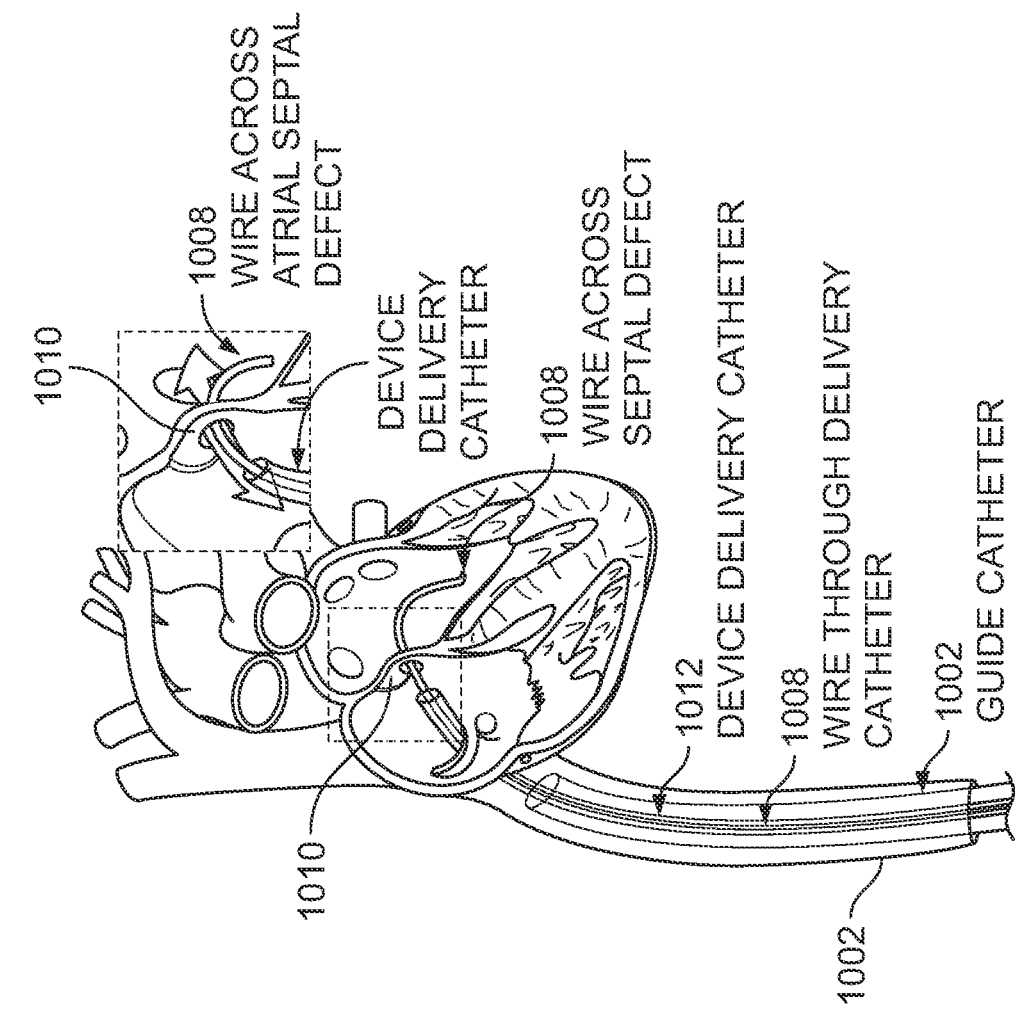
FIG. 10B illustrates a guide wire positioned across an ASD, in accordance with some embodiments of the present specification.
Figure 10A:
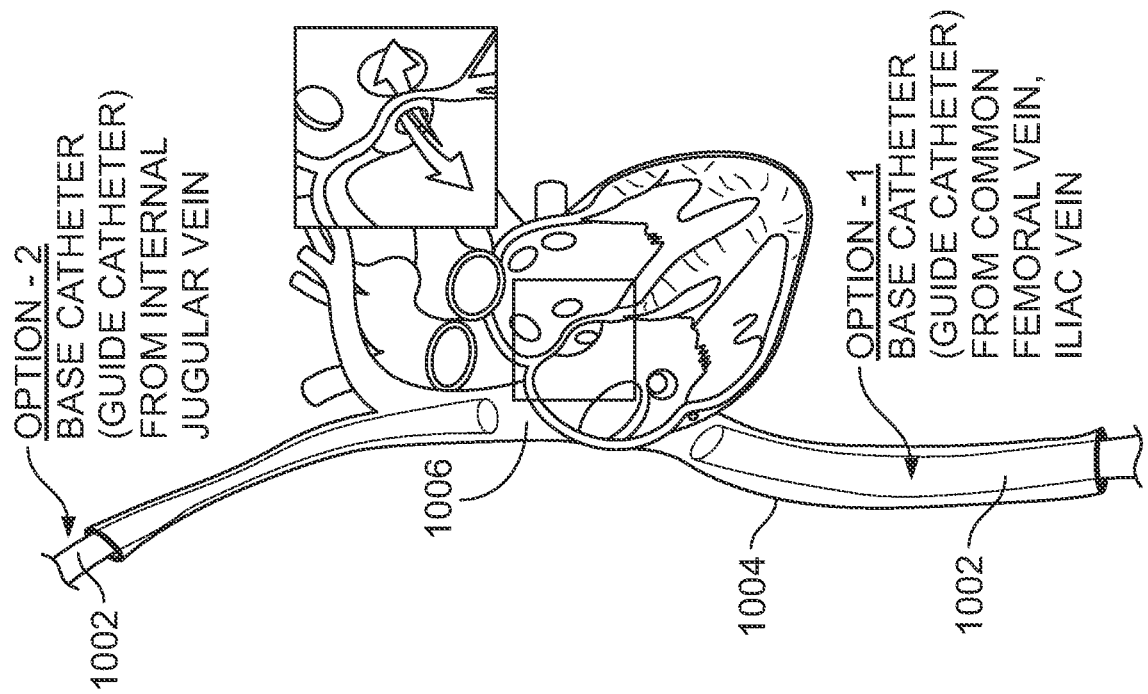
FIG. 10A illustrates a guide catheter positioned in the IVC or the SVC, in accordance with some embodiments of the present specification.

FIG. 9 is a flowchart of a plurality of exemplary steps of a method of using the closure device 700 to close, seal or occlude an atrial septal defect (ASD), in accordance with some embodiments of the present specification. At step 902, a base or guide catheter is positioned in either the inferior vena cava (IVC) through the femoral or iliac vein, or in the superior vena cava (SVC) via the cervical internal jugular vein. FIG. 10A illustrates a guide catheter 1002 positioned in the IVC 1004 or the SVC 1006.

At step 904, a guide wire is advanced through a delivery catheter and positioned across the ASD. In accordance with some aspects of the present specification, the guide wire remains across the ASD until closure of the ASD is accomplished and cure is confirmed. Consequently, access to the ASD is never lost. FIG. 10B illustrates a guide wire 1008 positioned across an ASD 1010. The guide wire 1008 is advanced through a delivery catheter 1012 that in turn is moved through the guide catheter 1002.

At step 906, the delivery catheter is advanced over the guide wire and across the ASD. FIG. 10C illustrates the delivery catheter 1012 advanced over the guide wire 1008 and positioned across the ASD 1010.

At step 908, the closure device is advanced over the guide wire and through the delivery catheter so that the closure device is positioned across the ASD. The closure device is positioned across the ASD such that a proximal element (of the closure device) lies in the right atrium and a distal element (of the closure device) lies in the left atrium. FIG. 10D illustrates the closure device 700 positioned across the ASD 1010 after having been advanced over the guide wire 1008 and through the delivery catheter 1012.

Figure 10F:
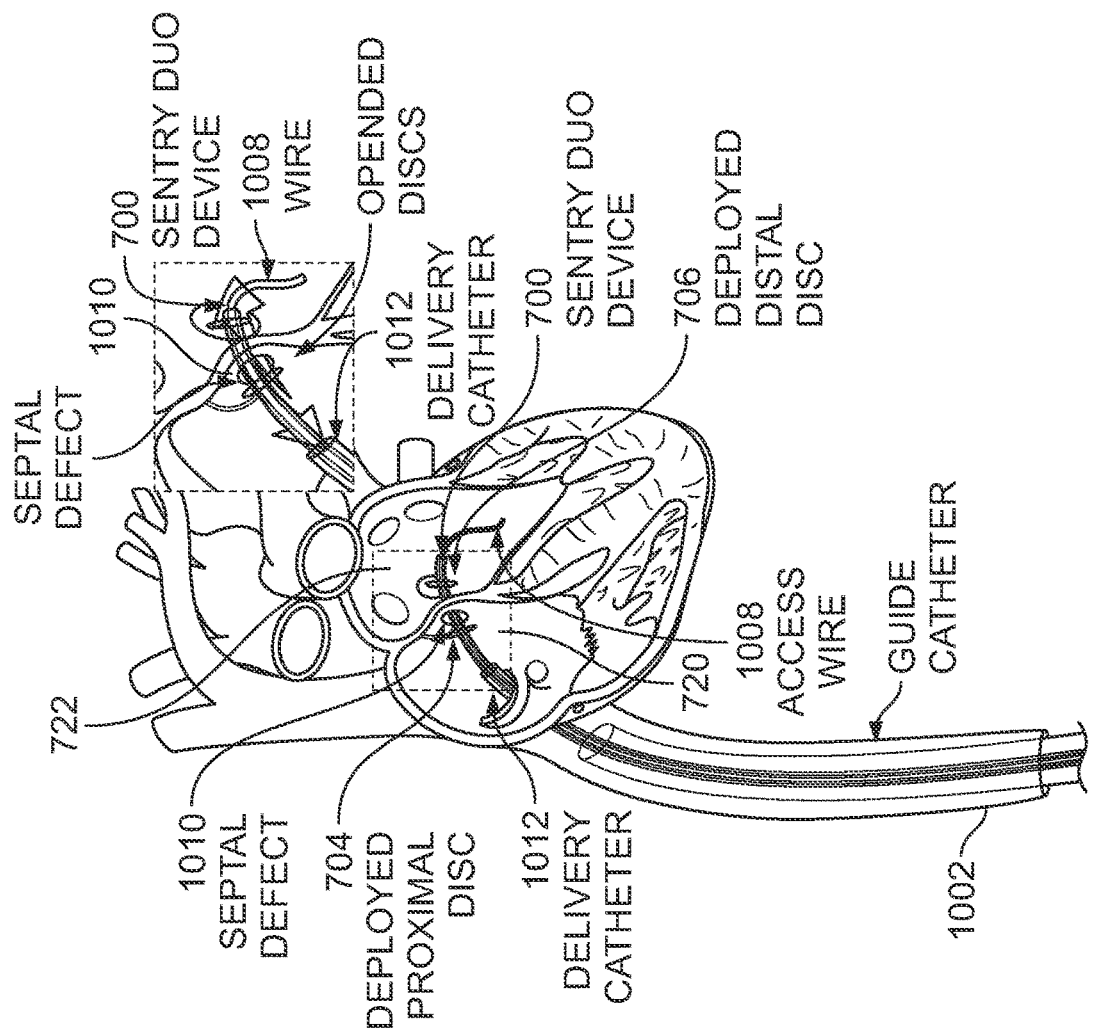
FIG. 10F illustrates the closure device with a proximal element deployed in the right atrium and a distal element deployed in the left atrium, in accordance with some embodiments of the present specification.
Figure 10E:
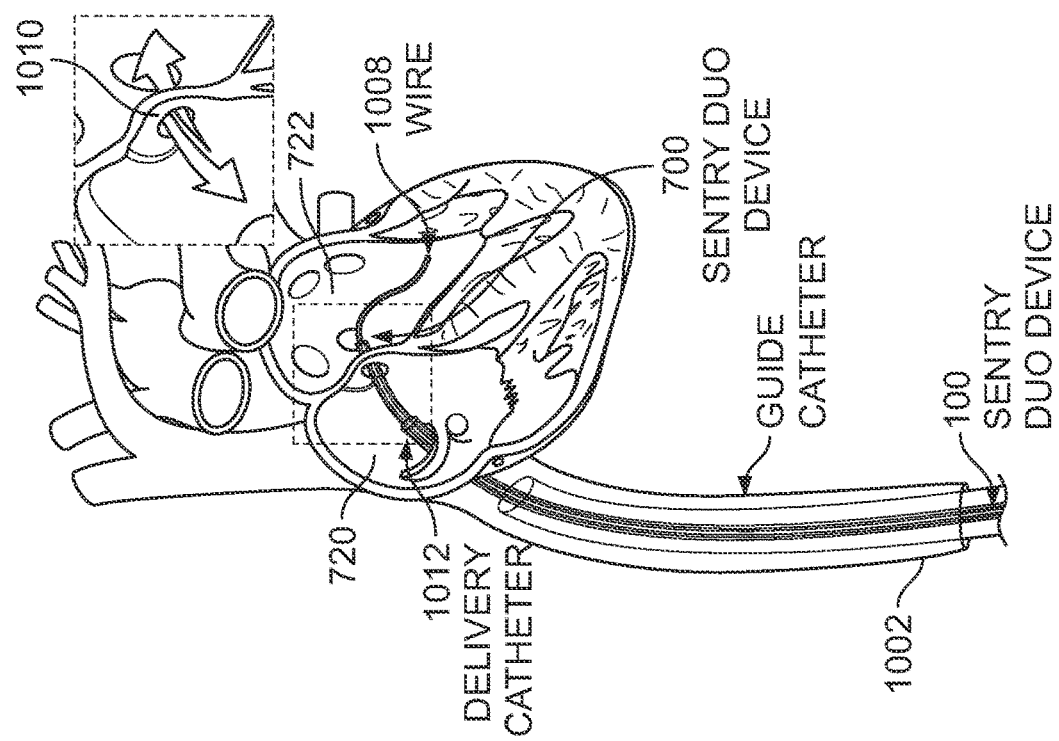
FIG. 10E illustrates the delivery catheter positioned in the right atrium, the closure device positioned across the ASD and the guide wire lying in the left atrium, in accordance with some embodiments of the present specification.

At step 910, the delivery catheter is retracted into the right atrium while the closure device is positioned across the ASD and the guide wire remains in the left atrium. FIG. 10E illustrates the delivery catheter 1012 positioned in the right atrium 720, the closure device 700 positioned across the ASD 1010 and the guide wire 1008 lying in the left atrium 722.

At step 912, the proximal and distal elements are deployed on either side of the ASD. Specifically, the proximal element is deployed at the right atrium side while the distal element is deployed at the left atrium side of the ASD. When deployed the proximal and distal elements have a first 3D geometric shape which, in some embodiments, is substantially spherical, elliptical or discoid. In some embodiments, the third interface 808 of the handle 802, as shown in FIG. 8, is used to deploy the proximal element into the first 3D geometric shape and the fourth interface 810 of the handle is used to deploy the distal element into the first 3D geometric shape. FIG. 10F illustrates the closure device 700 with a proximal element 704 deployed in the right atrium 720 and a distal element 706 deployed in the left atrium 722.

At step 914, the distal element is pulled back to cover the ASD on the left atrial side in order to occlude the ASD (on the left atrial side). The proximal element remains on the right atrial side of the ASD. At this stage, in some embodiments, the distal element transitions to a second 3D geometric shape such as, for example, a discoid. In embodiments, the fourth interface 810 of the handle 802, as shown in FIG. 8, is used to transition the distal element into the second 3D geometric shape. FIG. 10G illustrates the distal element 706 covering and occluding the ASD 1010 on the left atrial side while the proximal element 704 is positioned on the right atrial side of the ASD 1010.

At step 916, the proximal element is advanced against the right atrial side of the ASD in order to cover and occlude the ASD on the right atrial side. In embodiments, the first interface 804 of the handle 802, as shown in FIG. 8, is used to move the proximal element relative to the distal element to occlude the right atrial side of the atrial septal defect. At this stage, in some embodiments, the proximal element transitions to a second 3D geometric shape such as, for example, a discoid. In some embodiments, the third interface 808 of the handle 802, as shown in FIG. 8, is used to transition the proximal element into the second 3D geometric shape. The ASD is now closed, sealed or occluded by the proximal and distal elements. FIG. 10H illustrates the proximal element 704 covering or occluding the ASD 1010 on the right atrial side and the distal element 706 covering or occluding the ASD 1010 on the left atrial side.

It should be appreciated that, in some embodiments, the first and second geometric shapes are same for one or both the proximal and distal elements. In such embodiments, each of the first and second geometric shapes is discoid.

In some embodiments, a tip portion including the proximal element, distal element and an isthmus, connecting the proximal and distal elements, have a hydrogel coating to improve or enhance a watertight closure, sealing or occlusion of the ASD. The hydrogel swells or expands volumetrically in contact with fluid. The hydrogel serves to increase a surface volume of the closure device across the ASD thereby improving the quality of the fluid closure, seal or occlusion across the ASD.

At step 918, a locking device is advanced over the guide wire and crimped against the proximal element. The guide wire remains across the ASD ensuring that access is retained and not lost even after the ASD is occluded by the proximal and distal elements. FIG. 10I illustrates a locking nut 725 being advanced over the guide wire 1008 for crimping against the proximal element 704. The guide wire 1008 is positioned across the ASD 1010 which is occluded by the proximal and distal elements 704, 706.

With the guide wire and the guide catheter still in place, a contrasting or visualization agent may be injected in order to confirm and document closure of the ASD. Ultrasound can also be used, in some embodiments, to confirm closure of the ASD.

At step 920, the tip portion of the closure device, mounted with the proximal and distal elements, is detached or released with the proximal and distal elements occluding the ASD. In embodiments, the second interface 806 of the handle 802, as shown in FIG. 8, is used to release the tip portion from the first member of the closure device. The locking nut also remains in place. The guide wire, delivery catheter and guide catheter are removed from the patient's body once closure is confirmed. In some embodiments, when the guide wire is removed, the hydrogel on the isthmus swells and occludes any open space at the center of the isthmus thus eliminating any blood flow through a small open tunnel that remains when the guide wire is removed. FIG. 10J illustrates a tip portion 702 of the closure device 700 released in a position where the proximal and distal elements 704, 706 close, seal or occlude the ASD 1010 while the locking nut 725 remains in place against the proximal element 704. The guide wire 1008 and the catheters 1002, 1012 have been removed (and therefore not shown in FIG. 10J).

It should be appreciated that the closure device and the method of using the closure device to occlude a pathological connection or aperture between two anatomical structures provides a plurality of advantageous features, such as:

Use of a hydrogel coating to improve a watertight closure of the pathological connection;

A process of deploying the closure device to seal the pathological connection or aperture that does not require losing access across the pathological connection or aperture until cure is diagnosed using ultrasound and/or post device placement angiography (in case of ASDs);

Ability to close any pathologic connection between two anatomical structures such as, for example, atrial septal defect (ASD), gastrointestinal/enteric fistulas, genito/gyneco/urologic fistulas, and arteriovenous fistulas (AVF).

Vascular Closure Device

The present specification also discloses embodiments of a vascular closure device for sealing a puncture site in a patient's blood vessel and methods for using the various embodiments of the vascular closure device. In various embodiments, the closure device includes a tip having a proximal element and a distal element and a handle coupled to the tip through a plurality of telescoping tubes, wherein the handle includes at least one actuator to expand or collapse at least one of the proximal and distal elements, move the proximal elements relative to one another, and release the tip. In some embodiments, the proximal element is a PGLA (poly lactic-co-glycolic acid) plug spray-coated and impregnated with Genipin while the distal element is a tightly woven mesh of Nitinol. In some embodiments, each of the proximal and distal elements is a tightly woven mesh of Nitinol.

In some embodiments, the distal element optionally comprises PGLA, which may or may not be spray-coated and may optionally be impregnated with Genipin. In some embodiments, the PGLA based distal element may be left inside the patient's vessel lumen at the end of a closure procedure. In such embodiments, the PGLA based distal element is adapted to gradually be resorbed or dissolved into the body so as not to leave a foreign body inside the vessel over a long term.

The PGLA/Genipin based proximal element or distal element is a resorbable element that has an ability to crosslink fibrin allele groups thereby making it highly resistant to enzymatic degradation. The crosslinking also occurs between fibrin and surrounding tissues, proteins, in fat, external vessel walls, and muscle. This crosslinking provides thrombus and PGLA stability and reduces the likelihood of movement of the element(s) and potential displacement from an outer surface of the vessel puncture site.

In various embodiments, the distal element, composed of a tightly woven mesh of elastic material, such as Nitinol, expands within a vessel lumen thereby interrupting the flow of blood through a vessel puncture or access site. This differs from prior art devices that often use a balloon which may inadvertently puncture when used against calcified plaque rendering the device as having failed and therefore unusable. A ruptured balloon can also introduce air to the vascular system if the balloon is filled with air. In various embodiments, the closure device enables the sealing of puncture or access sites in any anatomic structure such as (but not limited to) cardiac structural defects (patent foramen *ovale*, septal wall defects, atrial appendages), arterio-venous fistulas, enteric fistulas, and organ perforations. It should be appreciated that the distal element may have a surface area defined by a mesh having interlaced wire defining a plurality of spaces or voids. In one embodiment, the total surface area of the voids is a value equal to or within any number ranging from 10% to 90% of the total surface area of the distal element.

Figure 11A:
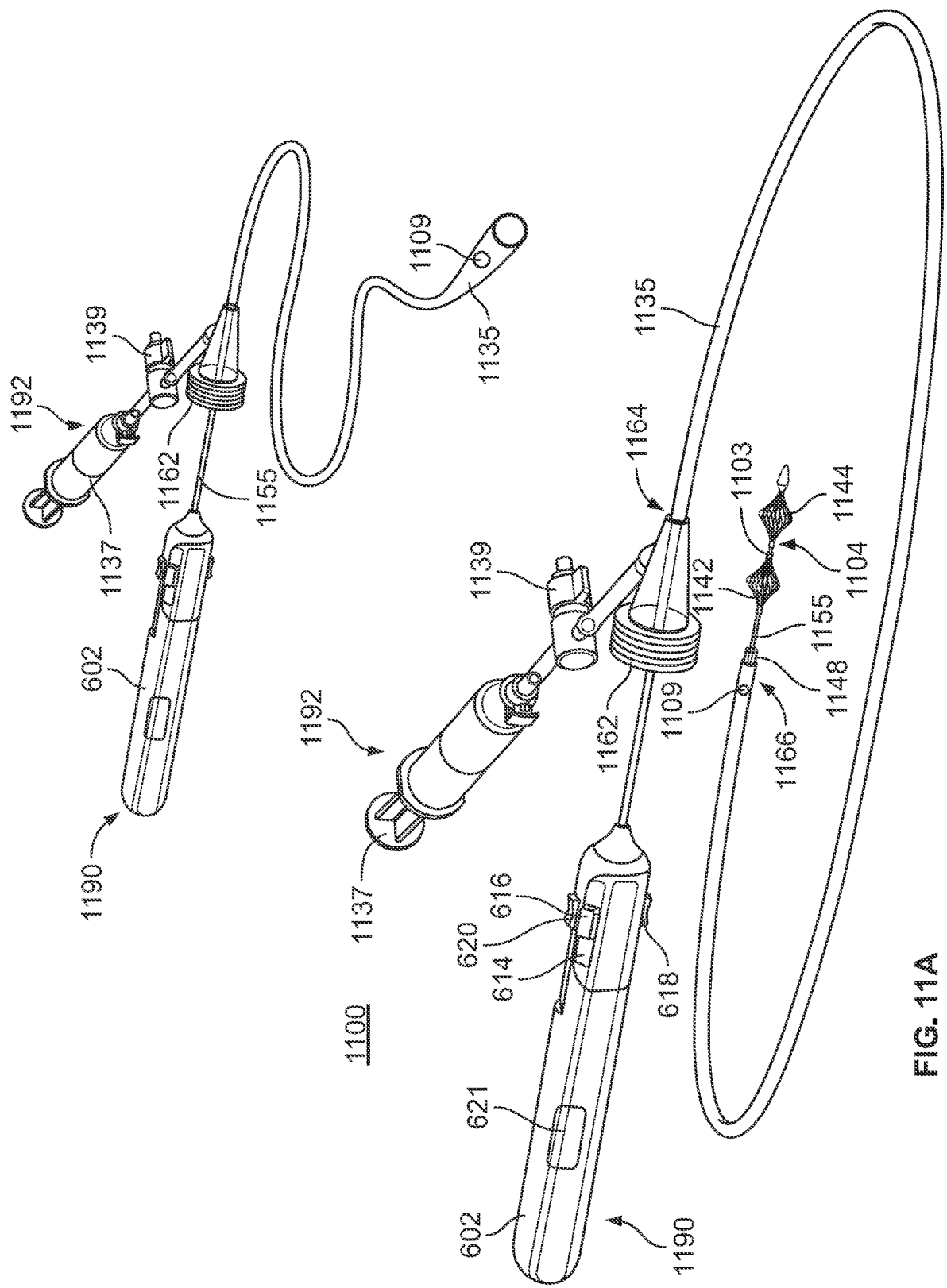
FIG. 11A is a perspective view of a vascular closure device, in accordance with an embodiment of the present specification.

FIG. 11A illustrates a vascular closure device 1100, in accordance with embodiments of the present specification. Vascular closure device 1100 is similar to the embodiments of the closure device 600 described with reference to FIG. 6 and is intended to close an opening or hole in a patient's blood vessel. The device 1100 comprises a first unit 1190 that includes a handle 602 coupled to a proximal end of a first member 1155, which in embodiments is an elongated or tubular member, having a plurality of telescoping tubes, such as at least four telescoping tubes, wherein a distal end of the elongated first member 1155 has a tip portion 1104. The handle 602 is configured to steer the tip portion 1104 in proximity to a puncture site in a patient's blood vessel. Tip portion includes a proximal element 1142 and a distal element 1144 connected by a second member 1103. In embodiments, the second member is a collapsible isthmus or bridge 1103. The handle 602 is further described in detail with reference to FIG. 8.

The device 1100 further comprises a second unit 1192 that includes an aspiration catheter 1135 having a suction source such as, for example, a syringe 1137, a one-way valve 1139 and a port 1162, where the port 1162 is coupled to a proximal end 1164 of the aspiration catheter 1135. In one embodiment, the one-way valve 1139 is configured to direct suction through the aspiration catheter 1135. For use during a procedure, the tip portion 1104 is placed into a delivery catheter 1148 and thereafter the delivery catheter 1148 is inserted into the aspiration catheter 1135, and follows through to port 1162, so that at least the tip portion 1104 projects distally from a distal end 1166 of the aspiration catheter 635.

In accordance with aspects of the present specification, the device 1100 is configured to enable an operator to single-handedly operate/actuate the handle portion 602 (using interfaces including first, second, third, and fourth physically manipulable interfaces such as, for example, knobs, levers or sliders 614, 616, 618, and 620), in order to mechanically expand, contract, or move a members of the distal end, as further discussed subsequently. A first interface integrated onto handle portion 602 enables proximal element 606 to move axially along isthmus or bridge 1103. A second interface integrated onto handle portion 602 enables uncoupling of tip portion 1104 from the elongated first member 1155 and the handle. Third and fourth interfaces integrated onto the handle portion 602 enable transition of the proximal and distal elements from substantially linear configurations into first expanded 3D geometric shapes and then, in some embodiments, into second 3D geometric shapes. In some embodiments, blood may be aspirated by actuating the hub 1139.

In accordance with some aspects of the present specification, the first and second units 1190, 1192 are manufactured as separate standalone units or devices. This is advantageous in that a physician may use the first unit 1190 with any third-party aspiration catheter. In some embodiments, the aspiration catheter 1135 is available with a plurality of external diameters such as, but not limited to, 12 Fr, 16 Fr, 20 Fr, and 24 Fr (where Fr represents French scale or gauge system). In some embodiments, the syringe 1137 has an exemplary, non-limiting, volume of 60 cubic centimeters.

In some embodiments, the closure device 1100 is designed for venous and arterial use with a maximum outer diameter of 26 French for the arterial vessels and 29 French for the venous vessels.

During operation of the device 1100, the tip portion 1104 is inserted into, for example, a blood vessel for performing a closure while the handle portion 602 remains in an operator/user's hands. While in some embodiments, the handle portion 602 includes four interfaces 614, 616, 618, 620 to manipulate the elements at the distal end, in alternate embodiments, fewer than four interfaces or greater than four interfaces may be used.

In some embodiments, at least one pressure transducer or sensor 1109 (such as, for example, a fiber-optic pressure sensor, electro-mechanical pressure sensor and hydraulic pressure sensor) is positioned at a distal end of aspiration catheter 1135. In some embodiments, the at least one pressure transducer or sensor 1109 is in the form of an elongated member that is co-extruded into the aspiration catheter 1135 so that the elongated member runs along a full length of the aspiration catheter 1135. In embodiments, the pressure transducer or sensor 1109 is in electrical communication with electronic circuitry located in the handle 602 of the first unit 1190. In embodiments, the handle 602 includes a pressure display 621. In various embodiments, the pressure transducer or sensor 1109 is configured to sense a pressure change or drop and, in particular, provide the physician with an indication that, as the puncture site in a patient's blood vessel is sealed, there is an associated change of pressure indicative of the closure.

First Embodiment

Proximal and Distal Elements

Referring to FIG. 11A, in some embodiments, the proximal element 1142 is a PGLA (poly lactic-co-glycolic acid) plug spray-coated and impregnated with Genipin. PGLA is a copolymer synthesized by means of ring-opening co-polymerization of two different monomers, the cyclic dimers (1,4-dioxane-2,5-diones) of glycolic acid and lactic acid. Genipin is a chemical compound found in Genipa americana fruit extract and is a natural cross-linker for proteins, collagen, gelatin, and chitosan cross-linking. It has a low acute toxicity with extremely high $LD_{50}$.

In some embodiments, the proximal element 1142, e.g. the PGLA-Genipin plug, is a resorbable element that has an ability to crosslink fibrin allele groups thus making it highly resistant to enzymatic degradation. The crosslinking also occurs between fibrin and surrounding tissues proteins in fat, external vessel walls, and muscle. This crosslinking provides thrombus and PGLA stability and reduces the likelihood of plug movement and displacement from a surface of a vessel puncture site.

In embodiments, the proximal element 1142 is pre-loaded on the tip 1104 prior to delivery of the closure device 1100 to a vessel puncture or access site. In some embodiments, the proximal element 1142 is free-floating on the tip 1104.

In some embodiments, the distal element 1144 is a mesh of tightly woven Nitinol. The distal element 1144 is configured to be in a non-expanded or collapsed state (substantially linear configuration) when outside a patient's vessel and to be in a first expanded 3D geometric shape or first deployed state and, in some embodiments, a second 3D geometric shape or second deployed when positioned inside the patient's vessel lumen. In some embodiments, the handle 602 includes at least one interface, knob, lever, button or slider 614/616/618/620 which when slid distally or forward towards the tip 1104 causes the distal element 1144 to be in the first expanded 3D geometric shape or first deployed state and then the second 3D geometric shape or second deployed state, and when slid proximally or backwards away from the tip 1104 causes the distal element 1144 to be in the non-expanded or collapsed state.

In some embodiments, the distal element 1144 has a three-dimensional (3D) shape when in the first expanded 3D geometric shape or first deployed state and when in the second 3D geometric shape or second deployed state. In some embodiments, the first expanded 3D geometric shape is substantially spherical, elliptical, or of an umbrella or chalice/cup and the second 3D geometric shape is discoid. In some embodiments, the distal element 1144 assumes a substantially cylindrical shape around tip 1104 when in the non-expanded or collapsed state.

In some embodiments, the distal element 1144 is of PGLA (which may or may not be spray-coated or impregnated with Genipin) so that the distal element 1144 may be left inside the patient's vessel lumen at the end of a closure procedure. In such embodiments, the PGLA based distal element 1144 is gradually resorbed.

In some embodiments, the vascular closure device 1100 is used to close a femoral puncture hole that ranges between 5 French and 28 French, wherein 1 French=0.33 mm. In some embodiments, the vascular closure device is used to cover and overlap a hole that has a diameter between 2 mm and 9 mm. In some embodiments, for closing a hole in a patient's blood vessel, the proximal element 1142 and distal element 1144, when in the first expanded 3D geometric shape and in the second 3D geometric shape, each have a diameter in a range of 5 mm to 13 mm. The second member 11003 is configured to collapse or retract toward 0 mm as the proximal element 11442 and distal element 1144 are drawn together to close the opening in the patient's vasculature. In embodiments, the second member is configured to span the thickness of a vascular wall before the proximal element and distal element are opposed to one another, thus sealing the hole. In embodiments, for closing a hole in a patient's blood vessel, the length of the second member ranges from 0.1 mm to 5 mm. In some embodiments, for closing a hole in a patient's blood vessel, the length of the second member is 3 mm.

Method of Use

Figure 11B:
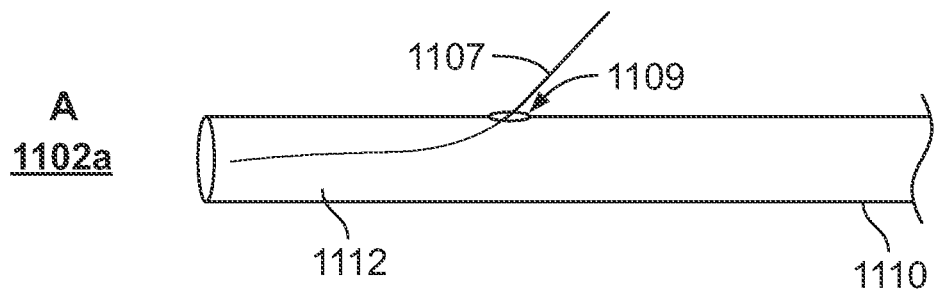
FIG. 11B is a pictorial representation of a plurality of exemplary steps of a method of performing a vascular closure procedure using a closure device, in accordance with some embodiments of the present specification.
Figure 11B:
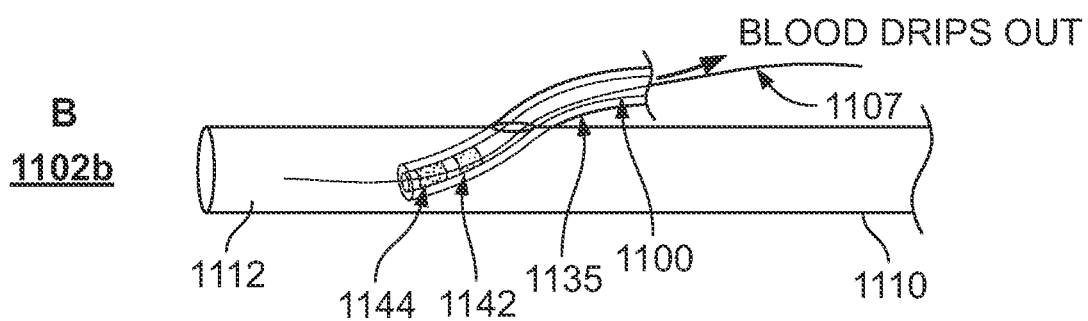
Figure 11B:
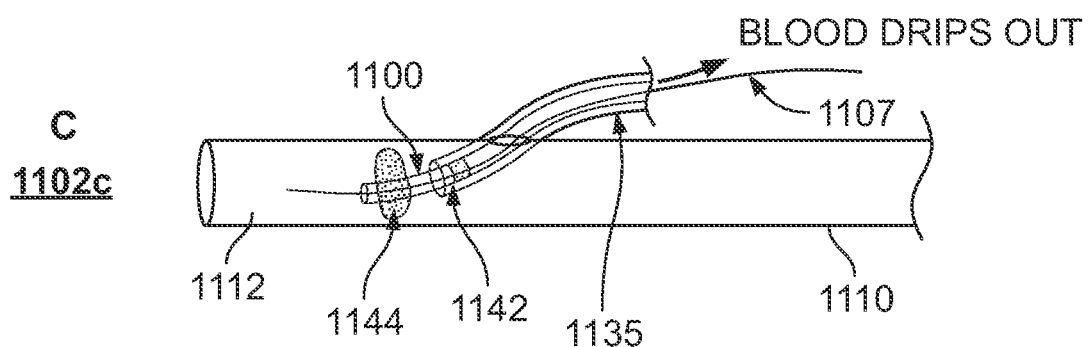
Figure 11B:
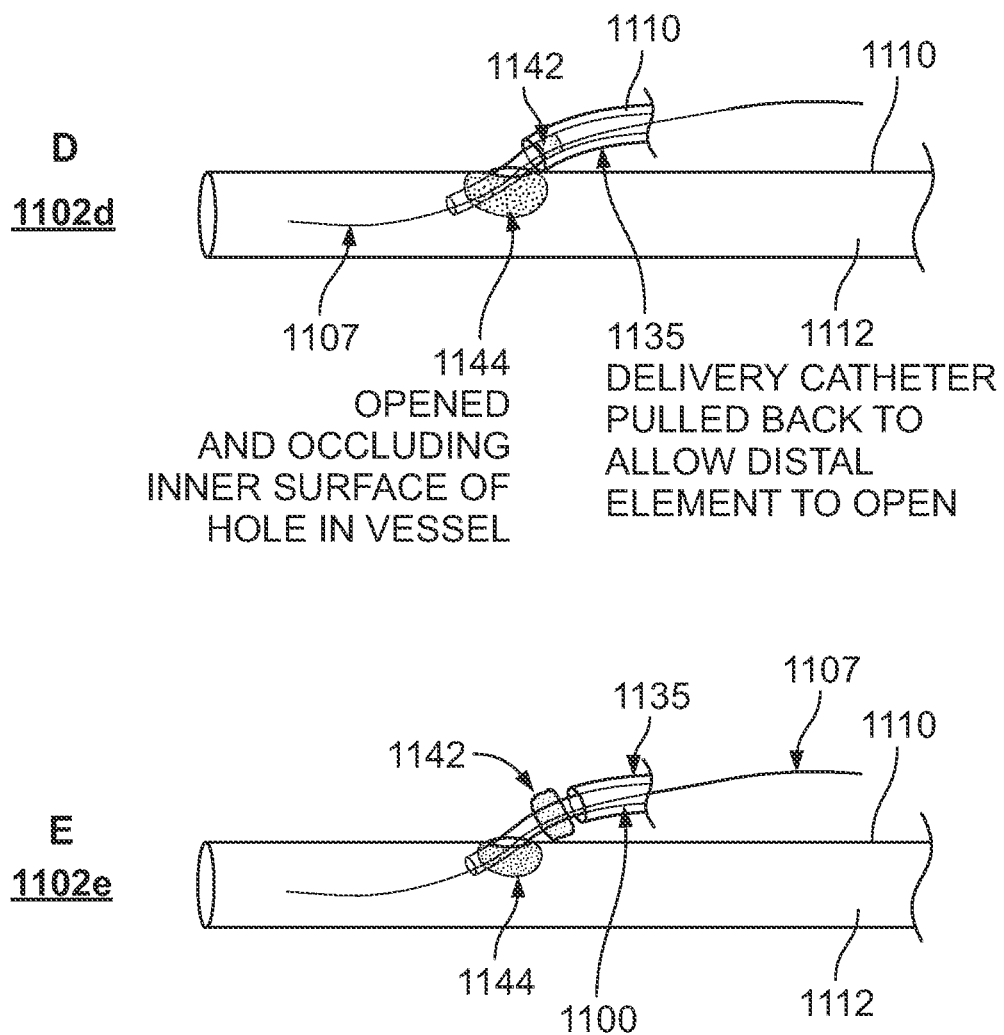
Figure 11B:
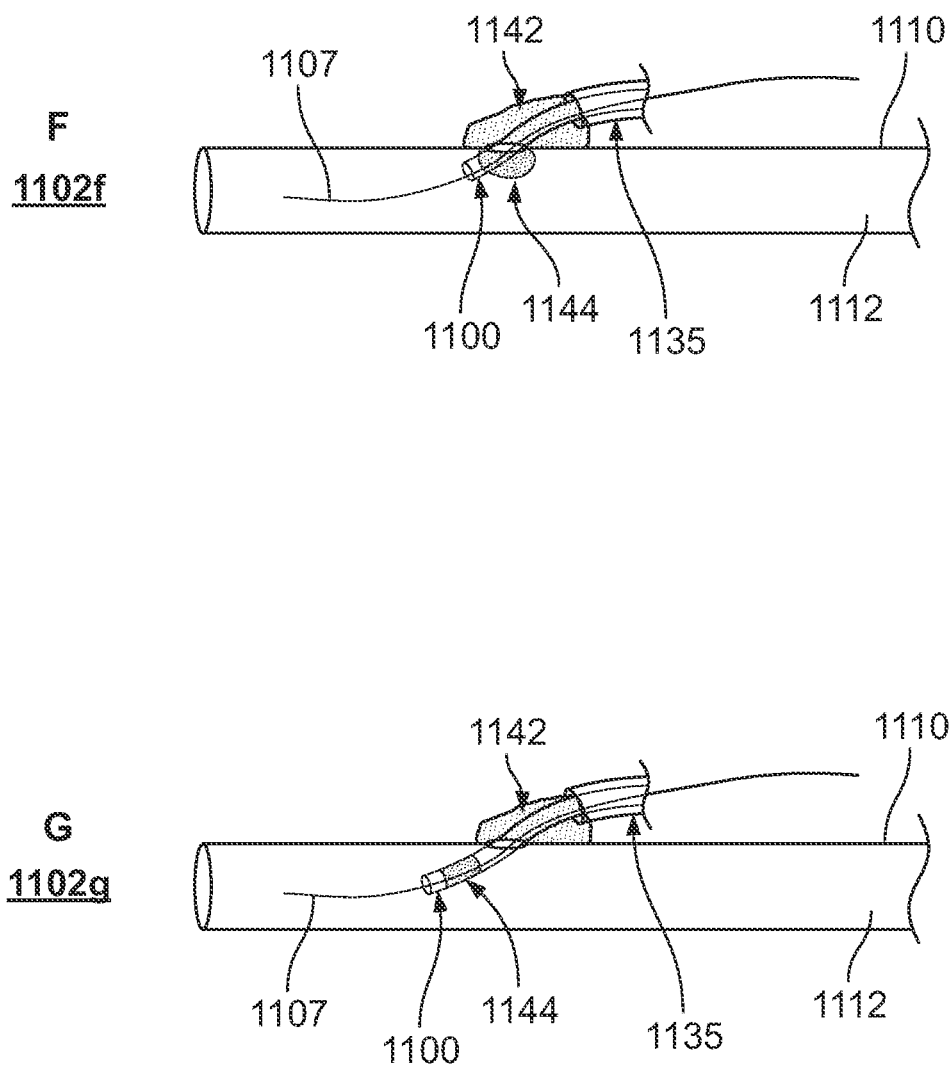
Figure 11B:
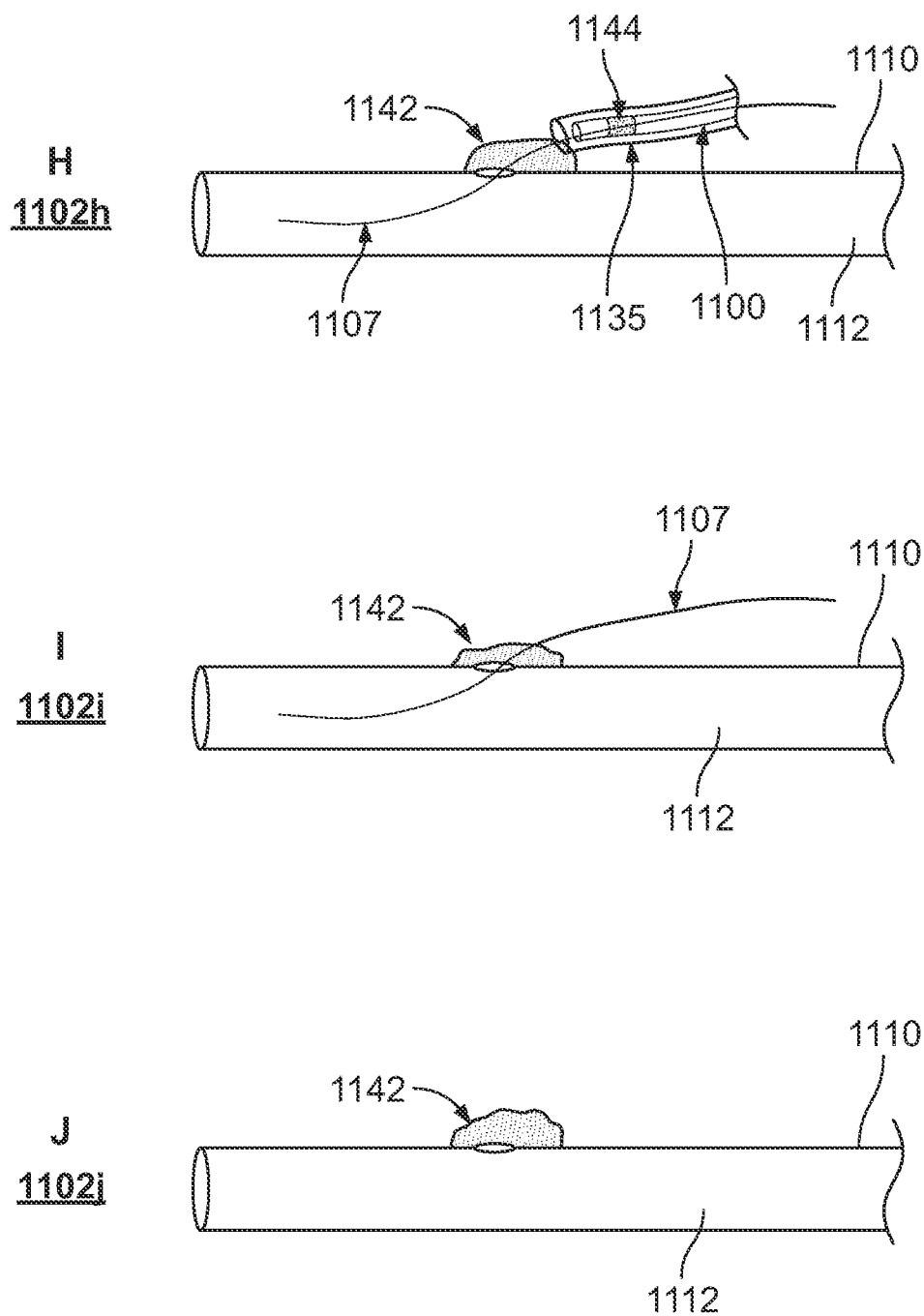
Figure 11C:
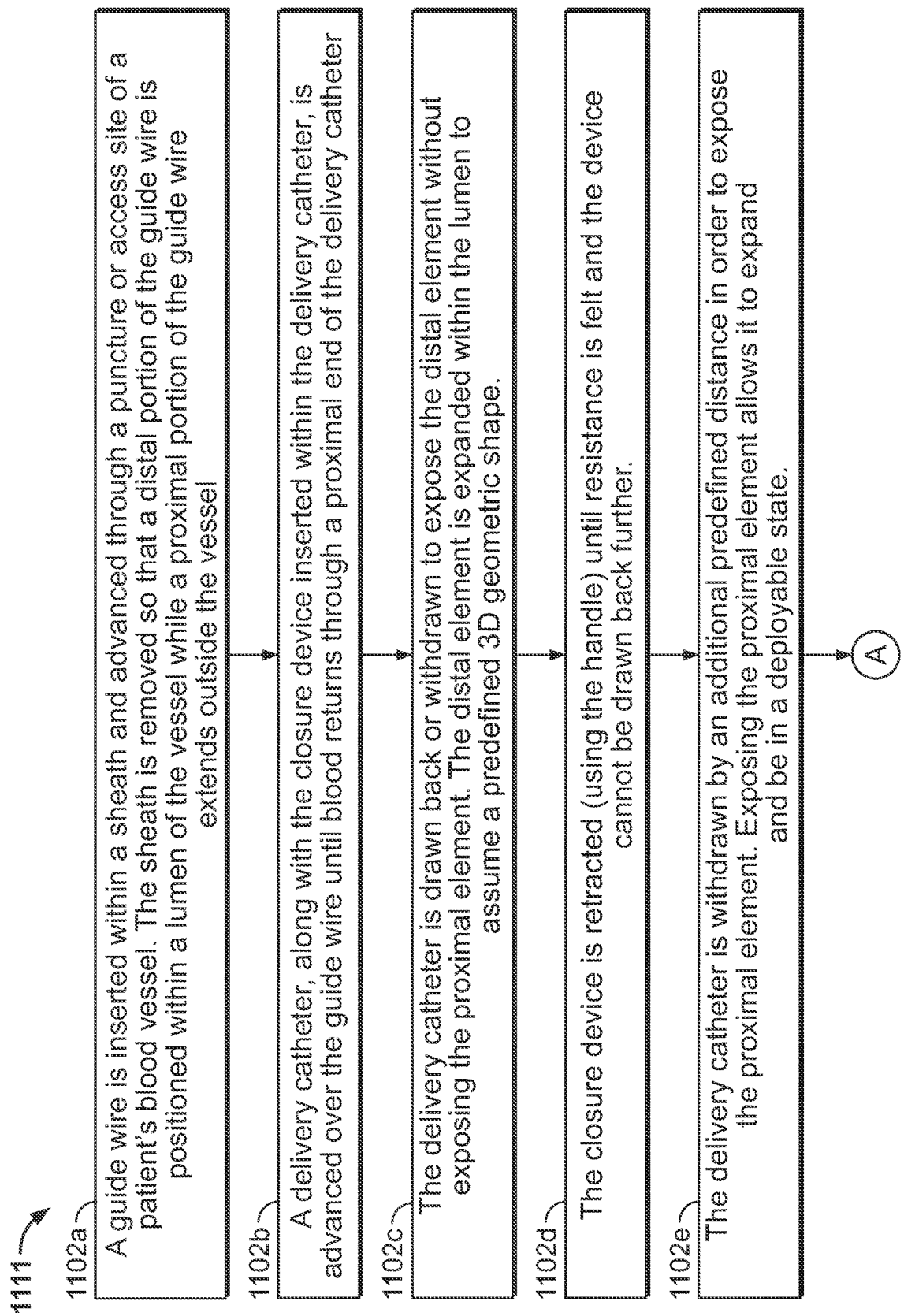
FIG. 11C is a flowchart of the plurality of exemplary steps of the method of FIG. 11B, in accordance with some embodiments of the present specification.

FIG. 11B shows a pictorial illustration while FIG. 11C is a flowchart of a plurality of exemplary steps of a method 1111 of performing a vascular closure procedure using a vascular closure device 1100, in accordance with some embodiments of the present specification. The closure device 1100 has a tip at a distal end and a handle at a proximal end to maneuver the tip, wherein the tip has a proximal element 1142 and a distal element 1144. The handle has a knob, lever, button, or slider to enable the distal element 1144 to be expanded or contracted. In some embodiments, the proximal element 1142 is a PGLA-Genipin plug. In some embodiments, the distal element 1144 is a tightly woven mesh of Nitinol and having a three-dimensional shape when in an expanded or deployed state.

Referring now to FIGS. 11B and 11C, at step 1102*a* a guide wire 1107 is inserted within a sheath and advanced through a puncture or access site 1109 of a patient's blood vessel 1110 so that a distal portion of the guide wire 1107 is positioned within a lumen 1112 of the vessel 1110. Thereafter, the sheath is removed leaving the distal portion of the guide wire 1107 within the lumen 1112 and a proximal portion of the guide wire 1107 extending outside the vessel 1110. In some embodiments, the guide wire 1107 has an outer diameter of 0.035 inches.

At step 1102*b*, in some embodiments, a delivery catheter 1135, along with the closure device 1100 inserted coaxially within the delivery catheter, is advanced over the guide wire 1107. Catheter 1135 is advanced until blood returns through a proximal end of the delivery catheter 1135 indicating that the tip of the closure device 1100 and a distal end of the delivery catheter are within the lumen 1112. In alternate embodiments, the delivery catheter 1135 is advanced over the guide wire 1107 until blood returns through the proximal end of the delivery catheter 1135 indicating that the distal end of the delivery catheter is within the lumen 1112. Thereafter, the closure device 1100 is inserted and advanced through the delivery catheter 1135 so that the tip of the closure device 1100 with the distal element 1144 also lies within the lumen 1112.

At this stage, the distal element 1144 is in a fully collapsed state. The proximal and distal elements 1142, 1144 lie within the delivery catheter 1135.

At step 1102*c*, the delivery catheter 1135 is drawn back or withdrawn to expose the distal element 1144 without exposing the proximal element 1142 (that is, the proximal element 1142 remains covered by the delivery catheter 1135). Blood still drips through the proximal end of the delivery catheter 1135 indicating that the tip of the closure device 1100 and the distal end of the delivery catheter 1135 are within the lumen 1112. In some embodiments, the delivery catheter 1135 is withdrawn by a predefined distance 'd'. In some embodiments, the predefined distance 'd' is 1 cm.

The knob, lever, button or slider of the handle is slid distally or forward towards the tip of the closure device 1100 causing the distal element 1144 to expand within the lumen 1112 and be deployed into a predefined three-dimensional shape having a desired outer diameter. In various embodiments, the predefined three-dimensional shape is spherical, chalice or cup, umbrella, or curved.

At step 1102*d*, the closure device 1100 is retracted, withdrawn or pulled back (using the handle) until resistance is felt and the device 1100 cannot be drawn back further. This indicates that the deployed distal element 1144 is in the lumen 1112 and occluding the puncture or access site 1109 of the vessel 1110 from inside the lumen 1112. Next, at step 1102*e*, the delivery catheter 1135 is drawn back or withdrawn by an additional predefined distance 'D' in order to expose the proximal element 1142. Exposing the proximal element 1142 allows the element 1142 to expand and be in a deployable state. In some embodiments, the additional predefined distance 'D' is approximately 2 cm.

At step 1102*f*, while keeping the distal element 1144 against an inner surface of the vessel 1110 which occludes the puncture or access site 1109 and stops blood from exiting the vessel 1110, the delivery catheter 1135 is advanced causing the distal end of the delivery catheter 1135 to push and compress the proximal element 1142 against an outer surface of the vessel 1110 and over the puncture or access site 1109. This position of the proximal and distal elements 1142, 1144, compressing the puncture or access site 1109 between them, is held for a few minutes to promote hemostasis. In one embodiment, the proximal and distal elements 1142, 1144 are held in this position for approximately 3 minutes.

At step 1102*g*, the proximal element 1142 is released from the delivery catheter 1135 over the puncture or access site 1109.

At step 1102*h*, the knob, lever, button or slider of the handle is slid proximally or away from the tip of the closure device 1100 causing the distal element 1144 to collapse or contract. The proximal element 1142 is still compressed against the outer surface of the vessel 1110 and over the puncture or access site 1109.

Thereafter, at step 1102*i*, the closure device 1100 along with the delivery catheter 1135 are withdrawn from the puncture or access site 1109. This results in stopping the dripping of blood from the proximal end of the delivery catheter 1135. Alternatively, in some embodiments, the closure device 1100 is first withdrawn leaving the delivery catheter 1135 in place and holding the proximal element 1142 in place against the outer vessel puncture site 1109. Thereafter, the delivery catheter 1135 is also withdrawn and removed from the vessel lumen 1112.

In accordance with some aspects of the present specification, the delivery catheter 1135 is removed at the end of the procedure and just prior to the final step (step 1102*j*)

which involves removal of the guide wire 1107. Since the delivery catheter 1135 remains in place, the user retains the ability to introduce additional substances and/or devices, into the puncture or access site 1109, prior to removal of the guide wire 1107 and procedure conclusion. In some embodiments, the additional substances may include prothrombotic agents such as gelatin, collagen paste, collagen slurry, additional Genipin, thrombin, etc. The user can also inject antibiotic at the end of the closure procedure to potentially reduce the risk of local infection.

Now, at step 1102j, the guide wire 1107 is also withdrawn and removed from the vessel lumen 1112 while the proximal element 1142 remains in place over the puncture or access site 1109. Finally, at step 1102k, manual pressure is applied over the proximal element 1142 and maintained for a predefined amount of time to promote hemostasis. In some embodiments, the manual pressure is maintained for about 3 minutes.

In accordance with some aspects of the present specification, the closure device 1100 functions over the guide wire 1107 at all times with the guide wire 1107 remaining in place for as long as the user wants it to remain in place across the puncture or access site 1109. As a result, unlike prior art closure devices, access to the vessel lumen is not lost. This means if the device 1100 fails to obtain hemostasis the user can perform additional closure procedures using the same in-place guide wire 1107.

Second Embodiment

Proximal and Distal Elements

Referring back to FIG. 11A, in some embodiments, a distal point of the proximal element 1142 and a proximal point of the distal element 1144 are coupled together and form a short waist (comprising second member 1103) between the proximal and distal elements 1142, 1144. In some embodiments, both the proximal and distal elements 1142, 1144 are made of PGLA spray coated and impregnated with Genipin. Genipin is useful due to its ability to crosslink to proteins thus improving thrombus strength and resistance to thrombosis and by securing the proximal and/or distal elements 1142, 1144 to surrounding proteins thus reducing their likelihood of shifting position over time. In some embodiments, both the proximal and distal elements 1142, 1144 are meshes of tightly woven Nitinol.

In some embodiments, the proximal and distal elements 1142, 1144 are configured to be in a) a non-expanded or collapsed state when both elements are outside a patient's vessel, b) a first expanded or deployed state when the distal element 1144 is positioned inside the patient's vessel lumen while the proximal element 1142 is positioned outside the patient's lumen at a puncture or access site and c) a second expanded state when the distal element 1144 is positioned inside the patient's vessel lumen while the proximal element 1142 is positioned outside the patient's lumen at a puncture or access site. In embodiments, a second volume of each of the proximal and distal elements 1142, 1144 when in the second expanded state is less than a first volume of each of the proximal and distal elements 1142, 1144 when in the first expanded state. In embodiments, a third volume of each of the proximal and distal elements 1142, 1144 when in the non-expanded state is less than a first volume of each of the proximal and distal elements 1142, 1144 when in the first expanded state.

In some embodiments, the handle 602 includes at least one knob, lever, button or slider 614/616/618/620 which when slid distally or forward towards the tip causes the proximal and distal elements 1142, 1144 to be in the first expanded or deployed state and when slid further distally or forward towards the tip causes the proximal and distal elements 1142, 1144 to be in the second expanded state.

In some embodiments, each of the proximal and distal elements 1142, 1144 assumes a substantially cylindrical shape around the tip 604 when in the non-expanded or collapsed state. In some embodiments, the proximal and distal elements 1142, 1144 each form a three-dimensional (3D) curved shape when in the expanded or deployed states. In some embodiments, the shape of the tip is that of a dumb-bell where each of the proximal and distal elements 1142, 1144 is substantially spherical. In some embodiments, each of the proximal and distal elements 1142, 1144 assumes a discoid or substantially disc shape when in the second expanded state.

In some embodiments, the distal element 1144 is of PGLA (which may or may not be spray-coated or impregnated with Genipin) so that the distal element 1144 may be left inside the patient's vessel lumen at the end of a closure procedure. In such embodiments, the PGLA based distal element 1144 is gradually resorbed so as not to leave a foreign body inside the vessel over a long term.

In some embodiments, the vascular closure device is used to close a femoral puncture hole that ranges between 5 French and 28 French, wherein 1 French=0.33 mm. In some embodiments, the vascular closure device is used to cover and overlap a hole that has a diameter between 2 mm and 9 mm. In some embodiments, for closing a hole in a patient's blood vessel, the proximal element 1142 and distal element 1144, when in the first expanded 3D geometric shape and in the second 3D geometric shape, each have a diameter in a range of 5 mm to 13 mm. The second member 1103 is configured to collapse or retract toward 0 mm as the proximal element 1142 and distal element 1144 are drawn together to close the opening in the patient's vasculature. In embodiments, the second member is configured to span the thickness of a vascular wall before the proximal element and distal element are opposed to one another, thus sealing the hole. In embodiments, for closing a hole in a patient's blood vessel, the length of the second member ranges from 0.1 mm to 5 mm. In some embodiments, for closing a hole in a patient's blood vessel, the length of the second member is 3 mm.

Method of Use

Figure 12B:
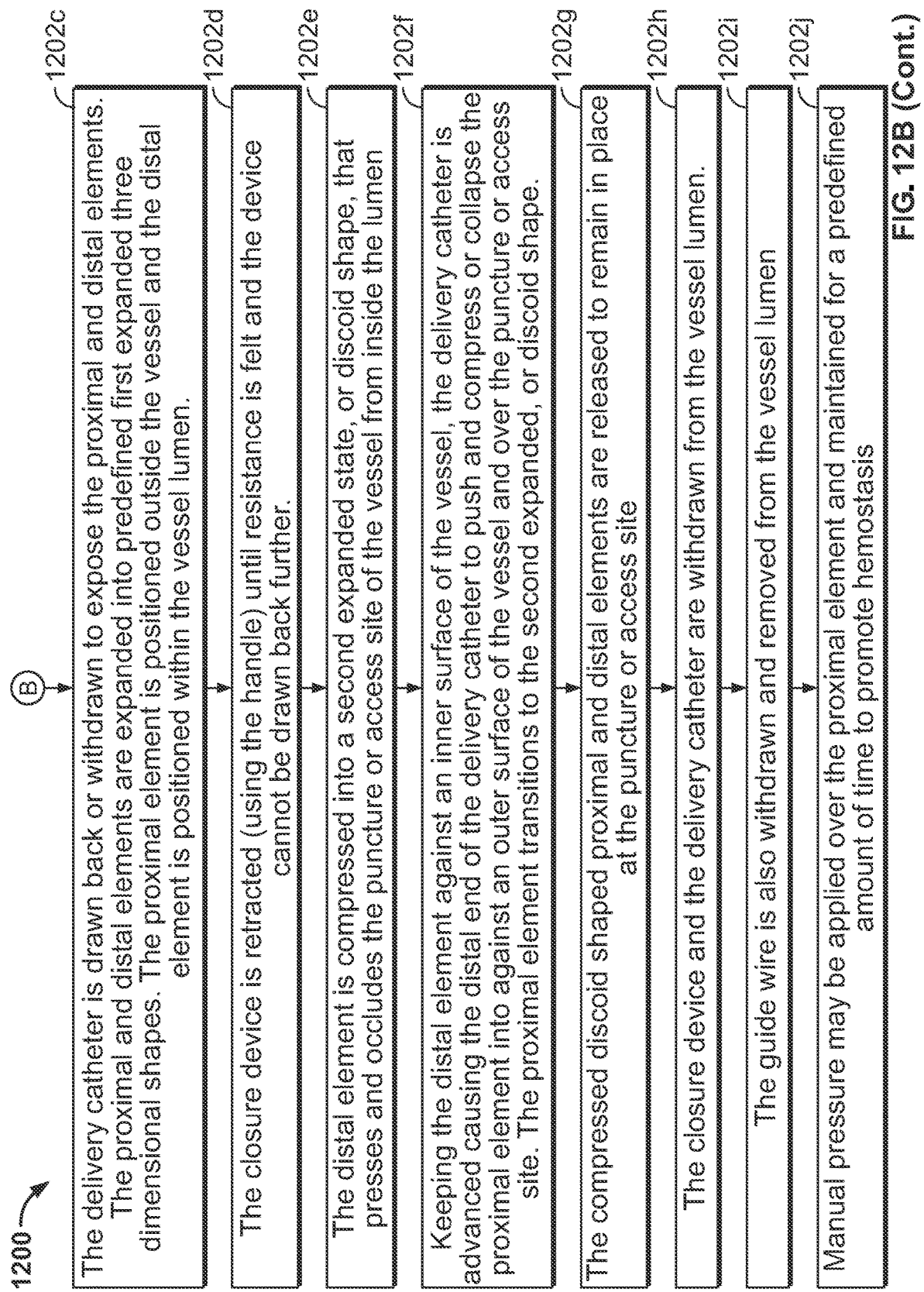
FIG. 12B is a flowchart of a plurality of exemplary steps of a method of performing a vascular closure procedure using the vascular closure device of FIG. 12A, in accordance with some embodiments of the present specification.

FIG. 12A illustrates a vascular closure device 1205 being used for performing a vascular closure procedure while FIG. 12B is a flowchart of a plurality of exemplary steps of a method 1200 of performing the vascular closure procedure using the vascular closure device 1205, in accordance with some embodiments of the present specification. The closure device 1205 has a tip at a distal end and a handle at a proximal end to maneuver the tip, wherein a distal point of a proximal element 1242 and a proximal point of a distal element 1244 are coupled together and form a waist or point of coupling 1250 (second member 1103 of FIG. 11A) between the proximal and distal elements 1242, 1244. In some embodiments, both the proximal and distal elements 1242, 1244 are made of PGLA spray-coated and impregnated with Genipin. In some embodiments, both the proximal and distal elements 1242, 1244 are meshes of tightly woven Nitinol.

The handle has a knob, lever, button or slider to enable the proximal and distal elements 1242, 1244 to be expanded or compressed. The proximal and distal elements 1242, 1244 together assume a dumb-bell shape with each element assuming a substantially spherical shape when in an expanded state.

In various embodiments, the method 1200 may be used for treating any undesired connection between two structures such as, but not limited to, structural heart defects (septal defects), arterio-venous fistulas, enteric fistulas and holes in any organ or anatomic entity, in addition to closing holes in a blood vessel puncture site.

Referring now to FIGS. 12A and 12B, at step 1202a a guide wire 1207 is inserted within a sheath and advanced through a puncture or access site 1209 of a patient's blood vessel 1210 so that a distal portion of the guide wire 1207 is positioned within a lumen 1212 of the vessel 1210. Thereafter, the sheath is removed leaving the distal portion of the guide wire 1207 within the lumen 1212 and a proximal portion of the guide wire 1207 extending outside the vessel 1210. In some embodiments, the guide wire 1207 has an outer diameter of 0.035 inches.

At step 1202b, in some embodiments, the delivery catheter 1214 is advanced over the guide wire 1207 until blood returns through the proximal end of the delivery catheter 1214 indicating that the distal end of the delivery catheter is within the lumen 1212. Thereafter, the closure device 1205 is inserted and advanced through the delivery catheter 1214 so that the waist 1250 (point of coupling between the proximal and distal elements 1242, 1244) is positioned at a level of the puncture or access site 1209. In some embodiments, the waist 1250 is visualized using a highly radio-opaque marker.

At this stage, the proximal and distal elements 1242, 1244 are in a fully collapsed state with the distal element 1244 lying within the lumen 1212 and the proximal element 1242 lying outside the lumen 1242 and over the puncture or access site 1209. The proximal and distal elements 1242, 1244 lie within the delivery catheter 1214.

At step 1202c, the delivery catheter 1214 is drawn back or withdrawn to expose the proximal and distal elements 1242, 1244. Blood still drips through the proximal end of the delivery catheter 1214 indicating that the distal element 1244 and the distal end of the delivery catheter 1214 are within the lumen 1212. In some embodiments, the delivery catheter 1214 is withdrawn by a predefined distance 'd'. In some embodiments, the predefined distance 'd' is 1 cm.

The knob, lever, button or slider of the handle is slid distally or forward towards the tip of the closure device 1205 causing the proximal and distal elements 1242, 1244 to expand and be deployed into a predefined first expanded three-dimensional shape having a desired outer diameter. In various embodiments, the predefined three-dimensional shape of the composite elements 1242, 1244 is dumb-bell wherein each of the elements 1242, 1244 is substantially spherical. At this stage, the proximal element 1242 is positioned outside the vessel 1210 and the distal element 1244 is positioned within the vessel 1210 or in the lumen 1212.

At step 1202d, the closure device 1205 is retracted, withdrawn or pulled back (using the handle) until resistance is felt and the device 1205 cannot be drawn back further. This indicates that the deployed distal element 1244 is in the lumen 1212 and occluding the puncture or access site 1209 of the vessel 1210 from inside the lumen 1212.

At step 1202e, the distal element 1244 is compressed into a second expanded state, or discoid shape, that presses and occludes the puncture or access site 1209 of the vessel 1210 from inside the lumen 1212. In some embodiments, the knob, lever, button or slider of the handle is slid proximally or away from the tip of the closure device 1205 to compress the distal element 1244 into the discoid shape.

At step 1202f, while keeping the distal element 1244 compressed into the discoid shape and pressed against an inner surface of the vessel 1210, which occludes the puncture or access site 1209 and stops blood from exiting the vessel 1210, the delivery catheter 1214 is advanced causing the distal end of the delivery catheter 1214 to push and compress the proximal element 1242 against an outer surface of the vessel 1210 and over the puncture or access site 1209. In some embodiments, the proximal element 1242 is compressed or collapsed into the second expanded state, or a discoid shape. This position of the proximal and distal elements 1242, 1244, compressing the puncture or access site 1209 between them thereby sealing the puncture or access site 1209, is held for a few minutes to promote hemostasis. In an embodiment, the proximal and distal elements 1242, 1244 are held in this position for approximately 3 minutes.

At step 1202g, the compressed discoid shaped proximal and distal elements 1242, 1244 are released to remain in place at the puncture or access site 1209.

Thereafter, at step 1202h, the closure device 1205 along with the delivery catheter 1214 are withdrawn from the puncture or access site 1209. This results in stopping the dripping of blood from the proximal end of the delivery catheter 1214. Alternatively, in some embodiments, the closure device 1205 is first withdrawn leaving the delivery catheter 1214 in place and holding the proximal element 1242 in place against the outer vessel puncture site 1209. Thereafter, the delivery catheter 1214 is also withdrawn and removed from the vessel lumen 1212.

In accordance with some aspects of the present specification, the delivery catheter 1214 is removed at the end of the procedure and just prior to the final step (step 1202i) which involves removal of the guide wire 1207. Since the delivery catheter 1214 remains in place, the user retains the ability to introduce additional substances and/or devices, into the puncture or access site 1209, prior to removal of the guide wire 1207 and procedure conclusion. In some embodiments, the additional substances may include prothrombotic agents such as gelatin, collagen paste, collagen slurry, additional Genipin, thrombin, etc. The user can also inject antibiotic at the end of the closure procedure to potentially reduce the risk of local infection.

Now, at step 1202i, the guide wire 1207 is also withdrawn and removed from the vessel lumen 1212 while the proximal and distal elements 1242, 1244 remain in place at the puncture or access site 1209. Finally, at step 1202j, manual pressure may be applied over the proximal element 1242 and maintained for a predefined amount of time to promote hemostasis. In some embodiments, the manual pressure is maintained for about 3 minutes.

In accordance with some aspects of the present specification, the closure device 1205 functions over the guide wire 1207 at all times with the guide wire 1207 remaining in place for as long as the user wants it to remain in place across the puncture or access site 1209. As a result, unlike prior art closure devices, access to the vessel lumen is never lost. This means if the device 1205 fails to obtain hemostasis the user can perform additional closure procedures using the same in-place guide wire 1207.

Third Embodiment

Proximal and Distal Elements

Figure 13A:
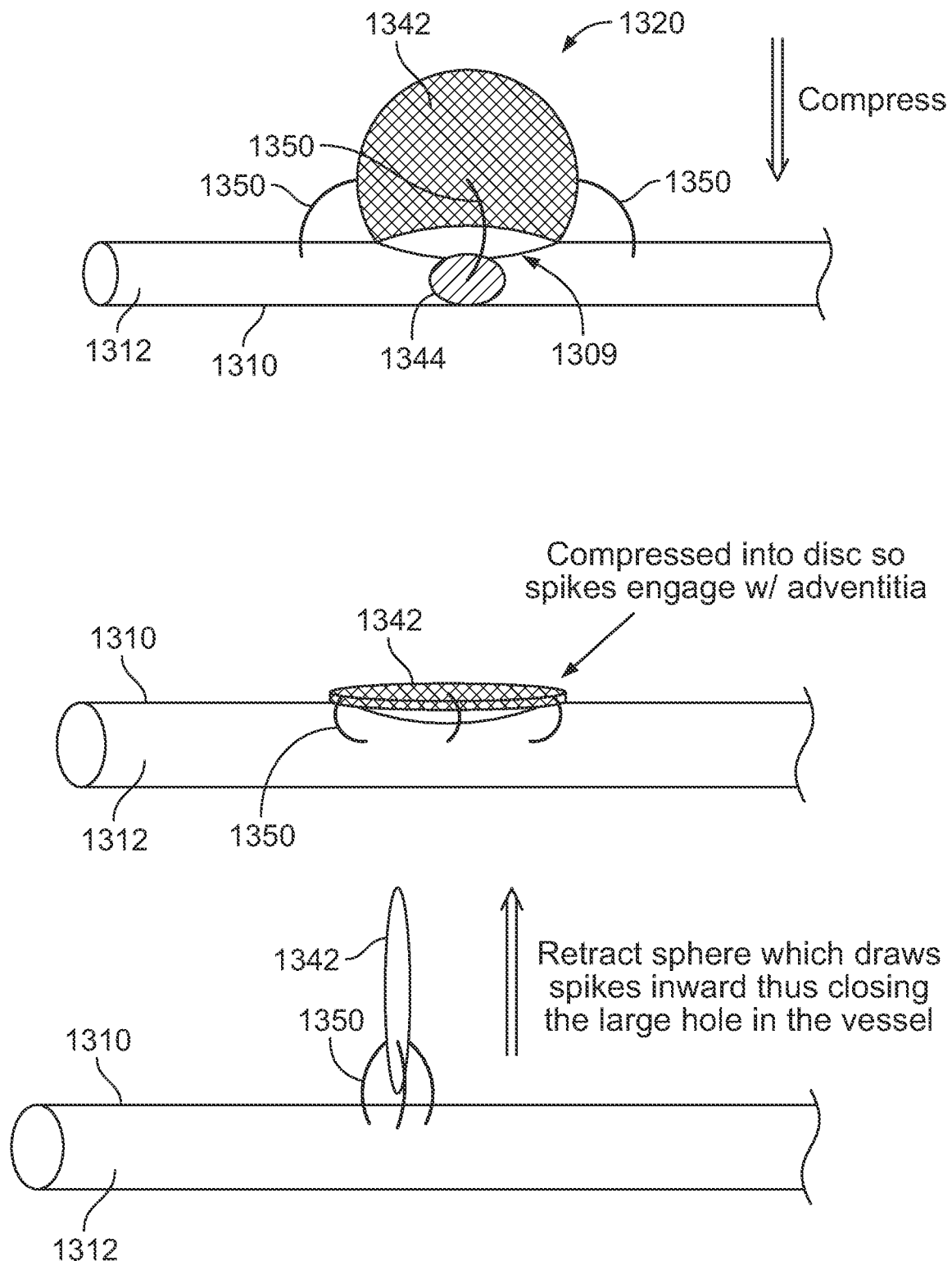
FIG. 13A illustrates a proximal element of a closure device, including barbs or spikes, when deployed for closing a puncture or access site in a patient's vessel, in accordance with some embodiments of the present specification.

Referring back to FIG. 11A, in some embodiments, the proximal element 1142 is a mesh of tightly woven Nitinol. In some embodiments, the proximal element 1142 is configured to be in a non-expanded or collapsed state when covered within the delivery catheter 1135 and in an expanded or deployed states when exposed outside the delivery catheter 1135. In some embodiments, the proximal element 1135 assumes a first expanded 3D geometric shape when in the expanded or deployed states. In some embodiments, the 3D geometric shape is substantially spherical. In some embodiments, the proximal element 1142 has a plurality of downward curving or bent barbs or spikes 1350, as shown in FIG. 13A, that protrude from a circumference that is at a predefined distance below a diameter of the proximal element 1142 when expanded to assume the substantially spherical shape.

In some embodiments, the distal element 1144 is a mesh of tightly woven Nitinol. The distal element 1144 is configured to be in a non-expanded or collapsed state when outside a patient's vessel and to be in expanded or deployed states when positioned inside the patient's vessel lumen. In some embodiments, the handle 602 includes at least one knob, lever, button or slider 614/616/618/620 which when slid distally or forward towards the tip 604 causes the distal element 1144 to be in the first or second expanded or deployed state and when slid proximally or backwards away from the tip 604 causes the distal element 1144 to be in the non-expanded or collapsed state.

In some embodiments, the distal element 1144 is a three-dimensional (3D) curved shape when in the expanded or deployed states. In some embodiments, the 3D curved shape is substantially spherical, discoid, umbrella or chalice/cup. In some embodiments, the distal element 1144 assumes a substantially cylindrical shape around the tip 604 when in the non-expanded or collapsed state.

In some embodiments, the distal element 1144 is of PGLA (which may or may not be spray-coated or impregnated with Genipin) so that the distal element 1144 may be left inside the patient's vessel lumen at the end of a closure procedure. In such embodiments, the PGLA based distal element 1144 is gradually resorbed so as not to leave a foreign body inside the vessel over a long period.

In some embodiments, the vascular closure device is used to close a femoral puncture hole that ranges between 5 French and 28 French, wherein 1 French=0.33 mm. In some embodiments, the vascular closure device is used to cover and overlap a hole that has a diameter between 2 mm and 9 mm. In some embodiments, for closing a hole in a patient's blood vessel, the proximal element 1142 and distal element 1144, when in the first expanded 3D geometric shape and in the second 3D geometric shape, each have a diameter in a range of 5 mm to 13 mm. The second member 1103 is configured to collapse or retract toward 0 mm as the proximal element 1142 and distal element 1144 are drawn together to close the opening in the patient's vasculature. In embodiments, the second member is configured to span the thickness of a vascular wall before the proximal element and distal element are opposed to one another, thus sealing the hole. In embodiments, for closing a hole in a patient's blood vessel, the length of the second member ranges from 0.1 mm to 5 mm. In some embodiments, for closing a hole in a patient's blood vessel, the length of the second member is 3 mm.

Method of Use

Figure 13B:
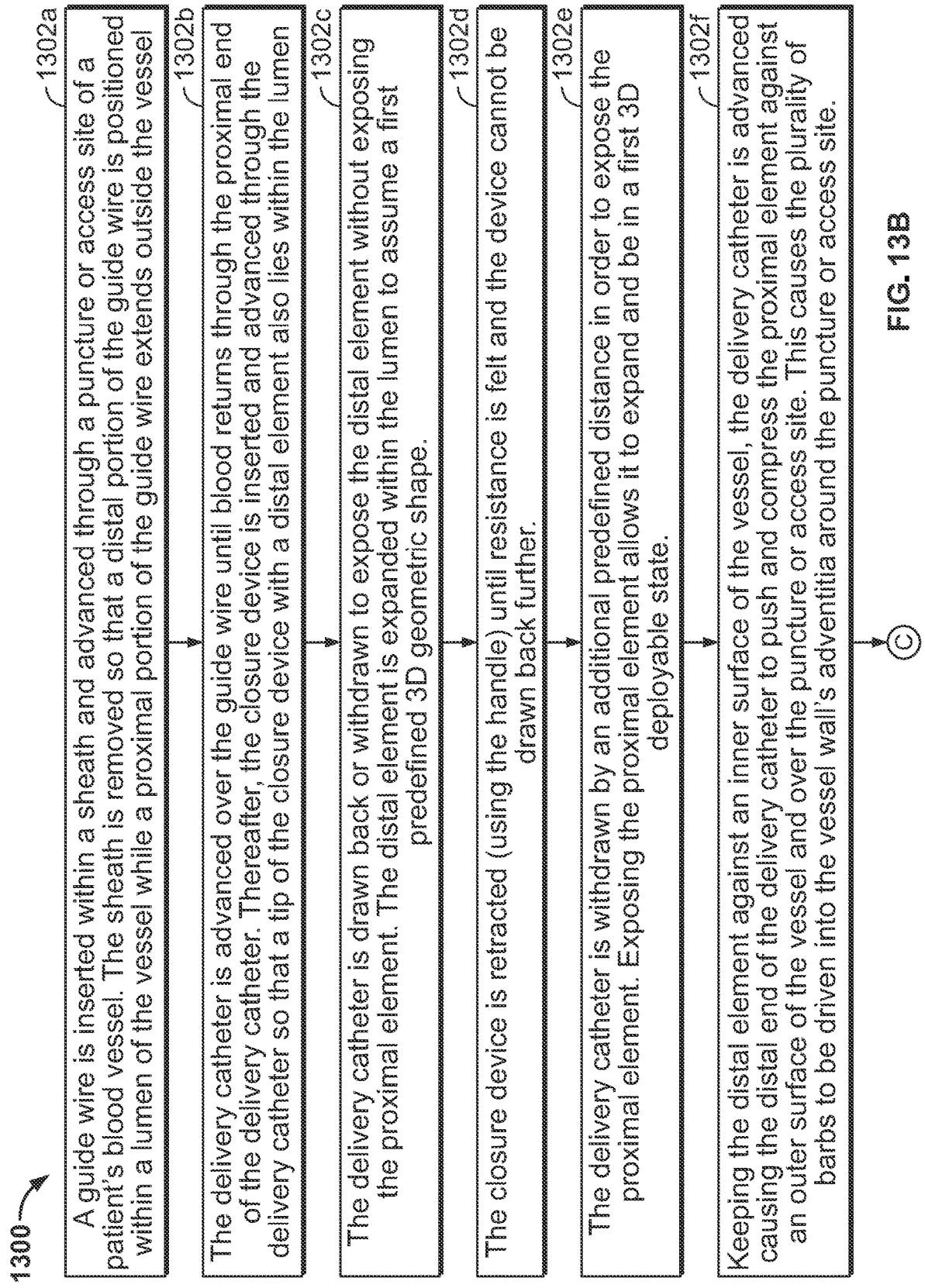
FIG. 13B is a flowchart of a plurality of exemplary steps of a method of performing a vascular closure procedure using a vascular closure device, in accordance with some embodiments of the present specification.
Figure 13B:
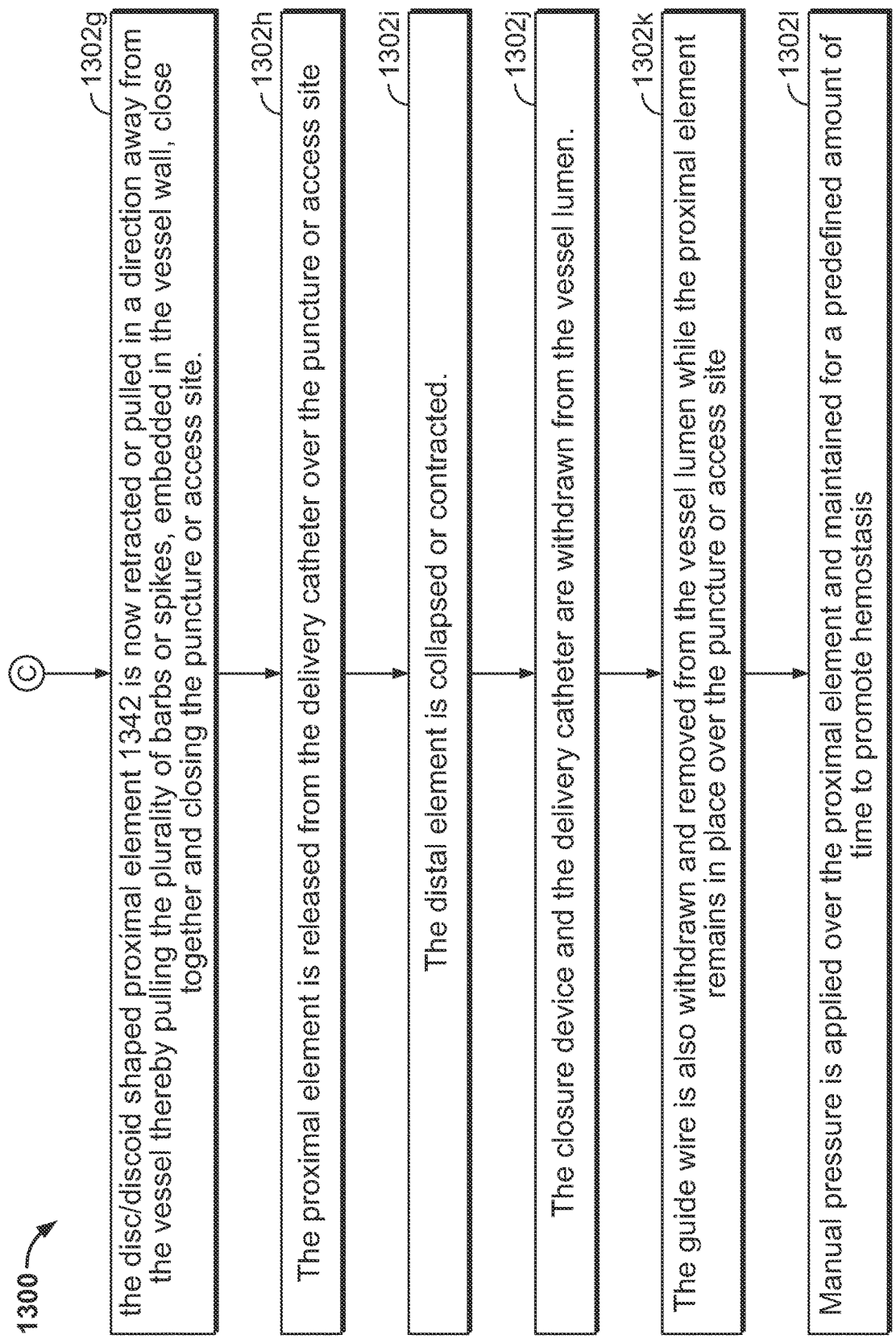

FIG. 13A illustrates a proximal element 1342 (having barbs or spikes 1350) of a vascular closure device 1320 being deployed for closing a puncture or access site 1309 in a patient's vessel 1310, while FIG. 13B is a flowchart of a plurality of exemplary steps of a method 1300 of performing a vascular closure procedure using the vascular closure device, in accordance with some embodiments of the present specification.

The closure device 1320 has a tip at a distal end and a handle at a proximal end to maneuver the tip, wherein the tip has a proximal element 1342 and a distal element 1344. The handle has a knob, lever, button or slider to enable the distal element 1344 to be expanded or contracted. In some embodiments, the proximal element 1342 is a tightly woven mesh of Nitinol. The proximal element 1342 is configured to be transitioned from a non-expanded or collapsed state to expanded or collapsed states, as described above with reference to FIG. 11A. In the first expanded state, the proximal element 1342 assumes a substantially spherical shape. In some embodiments, in the second expanded state, the proximal element 1342 assumes a discoid shape. In some embodiments, the proximal element 1342 has a plurality of downward curving or bent barbs or spikes 1350 that protrude from the substantially spherical shape along a circumference that is at a predefined distance below a diameter of the substantially spherical proximal element 1342. In some embodiments, the distal element 1342 is a tightly woven mesh of Nitinol and has a three-dimensional shape when in expanded or deployed states. In some embodiments, the 3D shape of distal element 1342 is substantially spherical, elliptical, umbrella or chalice/cup when in the first expanded state. In some embodiments, the 3D shape of the distal element 1342 is discoid in the second expanded state. In some embodiments, the distal element 1342 also includes barbs or spikes to physically engage an inner surface of a blood vessel.

In some embodiments, the closure device assists with the closure of large arterial puncture sites and when very large vascular access sheaths are used.

Referring now to FIGS. 13A and 13B, at step 1302a a guide wire is inserted within a sheath and advanced through a puncture or access site 1309 of a patient's blood vessel 1310 so that a distal portion of the guide wire is positioned within a lumen 1312 of the vessel 1310. Thereafter, the sheath is removed leaving the distal portion of the guide wire within the lumen 1312 and a proximal portion of the guide wire extending outside the vessel 1310. In some embodiments, the guide wire has an outer diameter of 0.014 inches.

At step 1302b, in some embodiments, a delivery catheter, along with the closure device is inserted within the delivery catheter, is advanced over the guide wire until blood returns through a proximal end of the delivery catheter indicating that the tip of the closure device and a distal end of the delivery catheter are within the lumen 1312. In alternate embodiments, the delivery catheter is advanced over the guide wire until blood returns through the proximal end of the delivery catheter indicating that the distal end of the delivery catheter is within the lumen 1312. Thereafter, the closure device is inserted and advanced through the delivery catheter so that the tip of the closure device with the distal element 1344 also lies within the lumen 1312.

At this stage, the proximal and distal elements 1342, 1344 are in fully collapsed states. The proximal and distal elements 1342, 1344 lie within the delivery catheter.

At step 1302c, the delivery catheter is drawn back or withdrawn to expose the distal element 1344 without exposing the proximal element 1342 (that is, the proximal element 1344 remains covered by the delivery catheter). Blood still drips through the proximal end of the delivery catheter indicating that the tip of the closure device and the distal end of the delivery catheter are within the lumen 1312. In some embodiments, the delivery catheter is withdrawn by a predefined distance 'd'. In some embodiments, the predefined distance 'd' is 1 cm.

The knob, lever, button or slider of the handle is slid distally or forward towards the tip of the closure device causing the distal element 1344 to expand within the lumen 1312 and be deployed into a predefined first three-dimensional shape having a desired outer diameter. In various embodiments, the predefined first three-dimensional shape is spherical, elliptical, chalice or cup, umbrella, or curved.

At step 1302d, the closure device is retracted, withdrawn or pulled back (using the handle) until resistance is felt and the device cannot be drawn back further. This indicates that the deployed distal element 1344 is in the lumen 1312 and occluding the puncture or access site 1309 of the vessel 1310 from inside the lumen 1312. Next, at step 1302e, the delivery catheter 1314 is drawn back or withdrawn by an additional predefined distance 'D' in order to expose the proximal element 1342. In some embodiments, the additional predefined distance 'D' is 2 cm. Exposing the proximal element 1342 allows the proximal element 1342 to expand and be in a first, 3D deployable state. In some embodiments, the proximal element expands into a 3D geometric shape. In some embodiments, the 3D geometric shape is substantially spherical.

At step 1302f, while keeping the distal element 1344 against an inner surface of the vessel 1310 which occludes the puncture or access site 1309 and stops blood from exiting the vessel 1310, the delivery catheter is advanced causing the distal end of the delivery catheter to push and compress the proximal element 1342 against an external adventitial surface of the vessel 1310 and over the puncture or access site 1309. The proximal element 1342 is eventually collapsed towards the vessel 1310 causing the proximal element 1342 to take a disc/discoid shape.

In some embodiments, the collapsed disc/discoid shaped proximal element 1342 is oriented such that its long axis is 180 degrees to the vessel wall (flat on top of the external surface of the vessel). When the proximal element 1342 collapses the plurality of barbs or spikes 1350 are driven into the vessel wall's adventitia that is located around the puncture or access site 1309 in the vessel 1310 thus securely attaching the proximal element 1342 to the vessel 1310. The barbs or spikes 1350 are curved downwards such that when they penetrate the adventitia they are less likely to pull out (like barbs).

At step 1302g, the disc/discoid shaped proximal element 1342 is now retracted or pulled in a direction away from the vessel 1310 so that the disc/discoid shaped proximal element 1342 is oriented substantially vertically (rather than horizontally as at step 1302f)—that is, the disc/discoid shaped proximal element 1342 is oriented at approximately 90 degrees to the vessel wall). This retraction process pulls the plurality of barbs or spikes 1350, embedded in the vessel wall, close together as the circumference of the disc/discoid shaped proximal element 1342 is reduced. This process closes the puncture or access site 1309 in the vessel 1310 as the circumferential edges of the puncture or access site 1309 are drawn together and slightly upward. In other words, retraction of the disc/discoid shaped proximal element 1342 causes the circumferential edges of the puncture or access site 1309 to be approximated and drawn slightly upwards thereby closing the puncture or access site 1309.

At step 1302h, the proximal element 1342 is released at the puncture or access site 1309.

At step 1302i, the knob, lever, button or slider of the handle is slid proximally or away from the tip of the closure device causing the distal element 1344 to collapse or contract. The proximal element 1342 is still compressed against the outer surface of the vessel 1310 and over the puncture or access site 1309.

Thereafter, at step 1302j, the closure device along with the delivery catheter are withdrawn from the puncture or access site 1309. This results in stopping the dripping of blood from the proximal end of the delivery catheter. Alternatively, in some embodiments, the closure device is first withdrawn leaving the delivery catheter in place and holding the proximal element 1342 in place against the outer vessel puncture site 1309. Thereafter, the delivery catheter is also withdrawn and removed from the vessel lumen 1312.

In accordance with some aspects of the present specification, the delivery catheter is removed at the end of the procedure and just prior to the final step (step 1302k) which involves removal of the guide wire. Since the delivery catheter remains in place, the user retains the ability to introduce additional substances and/or devices, into the puncture or access site 1309, prior to removal of the guide wire and procedure conclusion. In some embodiments, the additional substances may include prothrombotic agents such as gelatin, collagen paste, collagen slurry, additional Genipin, thrombin, etc. The user can also inject antibiotic at the end of the closure procedure to potentially reduce the risk of local infection.

Now, at step 1302k, the guide wire is also withdrawn and removed from the vessel lumen 1312 while the proximal element 1342 remains in place over the puncture or access site 1309. Finally, at step 1302l, manual pressure is applied over the proximal element 1342 and maintained for some time to promote hemostasis. In some embodiments, the manual pressure is maintained for about 3 minutes.

In accordance with some aspects of the present specification, the closure device functions over the guide wire at all times with the guide wire remaining in place for as long as the user wants it to remain in place across the puncture or access site 1309. As a result, unlike prior art closure devices, access to the vessel lumen is never lost. This means if the device fails to obtain hemostasis the user can perform additional closure procedures using the same in-place guide wire.

The above examples are merely illustrative of the many applications of the systems and methods of the present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A device for occluding an anatomical passage between a first anatomical structure and a second anatomical structure, the device comprising:
   a handle;
   a tip portion physically coupled to the handle through a first member and having a proximal element, a distal element, and a second member extending from the proximal element to the distal element, wherein the proximal element is movable axially along the second member of the tip portion and the distal element is not movable along the second member of the tip portion, and wherein each of the proximal element and the distal element is expandable from a substantially linear configuration to an expanded three-dimensional geometric shape which occupies a greater volume than the substantially linear configuration;
a first interface integrated into the handle, wherein, upon manipulating the first interface, the proximal element moves axially along the second member of the tip portion;
a second interface integrated into the handle, wherein, upon manipulating the second interface, the tip portion uncouples from the first member and the handle; and
a locking device configured to be passed over the first member and proximally attach to the tip portion such that it remains in place after the tip portion uncouples from the first member and the handle.

2. The device of claim 1, wherein the locking device is a nut configured to be crimped against the proximal element.

3. The device of claim 1, wherein, upon the tip portion uncoupling from the first member and the handle, at least one of the proximal element or the distal element proximal is configured to change from the expanded three-dimensional geometric shape to a second three-dimensional geometric shape and wherein the second three-dimensional geometric shape occupies a smaller volume than the expanded three-dimensional geometric shape.

4. The device of claim 3, wherein the second three-dimensional geometric shape is substantially discoidal and the expanded three-dimensional geometric shape is substantially spherical or elliptical.

5. The device of claim 1, wherein the first interface and the second interface is a button or slider.

6. The device of claim 1, wherein the second member comprises corrugated walls configured to collapse when the proximal element is moved distally.

7. The device of claim 1, wherein the second interface is configured to release the tip portion using at least one of a mechanical, electrolytic or thermal release system.

8. The device of claim 1, wherein at least one of the proximal element, the distal element and the second member are coated with a hydrogel.

9. The device of claim 1, wherein the second member is coated with a hydrogel adapted to swell to assist in the occlusion of the anatomical passage.

10. The device of claim 1, further comprising a guide wire, wherein the catheter is configured to be advanced over the guide wire for enabling the tip portion to lie across the anatomical passage.

11. A method of occluding an atrial septal defect, comprising:
providing a device, wherein the device comprises:
a handle;
a tip portion physically coupled to the handle through a first member and having a proximal element, a distal element, and a second member extending from the proximal element to the distal element, wherein only one of the proximal element or distal element is movable axially along the second member of the tip portion with a remaining one of the proximal element or distal element being fixed, and wherein each of the proximal element and the distal element is expandable from a substantially linear configuration to an expanded three-dimensional geometric shape which occupies a greater volume than the substantially linear configuration;
a first interface integrated into the handle, wherein, upon manipulating the first interface, the proximal element moves axially along the second member of the tip portion; and
a second interface integrated into the handle, wherein, upon manipulating the second interface, the tip portion detaches from the first member and the handle; and
advancing a guide wire to position the guide wire across the atrial septal defect into a left atrium;
advancing a delivery catheter over the guide wire to position the delivery catheter across the atrial septal defect and into the left atrium;
advancing the device over the guide wire and through the delivery catheter to position the tip portion of the device across the atrial septal defect;
deploying the proximal element in the right atrium side and the distal element in the left atrium side of the atrial septal defect;
positioning the distal element to occlude the atrial septal defect on the left atrial side;
using the first interface, moving the proximal element relative to the distal element to occlude the right atrial side of the atrial septal defect;
advancing a locking device over the guide wire against the proximal element; and
using the second interface, releasing the tip portion from the first member, thereby leaving the proximal element, second member, and distal element in place to occlude the atrial septal defect.

12. The method of claim 11, further comprising removing the guide wire, delivery catheter, and first member after leaving the proximal element, second member, and distal element in place to occlude the atrial septal defect.

13. The method of claim 11, further comprising removing the guide wire, delivery catheter, and first member after confirming occlusion of the atrial septal defect using contrast.

14. The method of claim 11, wherein advancing the locking device over the guide wire against the proximal element comprises advancing a nut over the guide wire and crimping the nut against the proximal element.

15. The method of claim 11, wherein positioning the distal element to occlude the atrial septal defect on the left atrial side comprises retracting the delivery catheter into a right atrium.

16. The method of claim 11, wherein, upon releasing the tip portion from the first member, at least one of the proximal element or the distal element proximal is configured to change from the expanded three-dimensional geometric shape to a second three-dimensional geometric shape and wherein the second three-dimensional geometric shape occupies a smaller volume than the expanded three-dimensional geometric shape.

17. The method of claim 16, wherein the second three-dimensional geometric shape is substantially discoidal and the expanded three-dimensional geometric shape is substantially spherical or elliptical.

18. The method of claim 11, wherein the second member comprises corrugated walls configured to collapse when the proximal element is moved distally.

19. The method of claim 11, wherein the second interface is configured to release the tip portion using at least one of a mechanical, electrolytic or thermal release system.

20. The method of claim 11, wherein at least one of the proximal element, the distal element and the second member are coated with a hydrogel adapted to swell to assist in the occlusion of the atrial septal defect.

* * * * *